(12) United States Patent
Kawamura et al.

(10) Patent No.: US 7,598,667 B2
(45) Date of Patent: Oct. 6, 2009

(54) ARYLAMINE COMPOUND AND ORGANIC ELECTROLUMINESCENCE DEVICE CONTAINING THE SAME

(75) Inventors: Hisayuki Kawamura, Sodegaura (JP); Tetsuya Inoue, Sodegaura (JP); Chishio Hosokawa, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 397 days.

(21) Appl. No.: 10/556,430

(22) PCT Filed: Apr. 26, 2004

(86) PCT No.: PCT/JP2004/006006
§ 371 (c)(1), (2), (4) Date: Nov. 9, 2005

(87) PCT Pub. No.: WO2004/101491
PCT Pub. Date: Nov. 25, 2004

(65) Prior Publication Data
US 2007/0018569 A1 Jan. 25, 2007

(30) Foreign Application Priority Data
May 15, 2003 (JP) ............................. 2003-136710

(51) Int. Cl.
H01L 51/54 (2006.01)
H05B 33/14 (2006.01)
C09K 11/06 (2006.01)
C07C 211/60 (2006.01)

(52) U.S. Cl. ................... 313/504; 313/506; 428/690; 428/917; 564/308; 257/40; 257/E51.047

(58) Field of Classification Search ............... None
See application file for complete search history.

(56) References Cited

U.S. PATENT DOCUMENTS 5,098,809 A    3/1992  Kikuchi et al. ............ 430/73
5,378,519 A *  1/1995  Kikuchi et al. ............ 428/690
5,840,217 A * 11/1998  Lupo et al. ................ 252/583
5,932,383 A *  8/1999  Nakata et al. ........... 430/58.75
6,379,590 B1   4/2002  Wu et al.
6,515,182 B2 * 2/2003  Hosokawa et al. .......... 564/427
6,784,452 B2 * 8/2004  Toguchi et al. ............ 257/40
6,822,094 B2 *11/2004  Salbeck et al. ........... 544/230
2002/0037429 A1* 3/2002  Sato et al. ................ 428/690

FOREIGN PATENT DOCUMENTS

| EP | 0 449 741 | 10/1991 |
| EP | 0 823 669 A1 | 2/1998 |
| EP | 0 879 868 | 11/1998 |
| JP | 06-102683 | 4/1994 |
| JP | 06102683 A * | 4/1994 |
| JP | 11 184109 | 7/1999 |
| JP | 11184119 A * | 7/1999 |
| JP | 2002-359079 | 12/2002 |
| JP | 2004-004290 | 1/2004 |

OTHER PUBLICATIONS

JP 11-184119, Nakada et al., machine translation.*
JP 06-102683, Kikuchi et al., machine translation.*
"Organic EL Device Development Strategy," Next Generation Display Device Institute, Jun. 30, 1992, Science Forum Corporation (publisher Hirotaka Motoyama).

* cited by examiner

*Primary Examiner*—D. Lawrence Tarazano
*Assistant Examiner*—Brett A Crouse
(74) *Attorney, Agent, or Firm*—Steptoe & Johnson LLP

(57) ABSTRACT

Arylamine compounds having at least one spiro bond are provided to the layers of an electroluminescent device. The compounds act as hole transporting and luminescent host materials for both fluorescent and phosphorescent emission. Electroluminescent devices employing the arylamine compounds exhibit excellent luminous efficiency, heat resistance and device life.

10 Claims, No Drawings

ARYLAMINE COMPOUND AND ORGANIC ELECTROLUMINESCENCE DEVICE CONTAINING THE SAME

CLAIM OF PRIORITY

This application claims priority under 35 USC 371 to International Application No. PCT/JP2004/006006, filed on Apr. 26, 2004, which claims priority to Japanese Patent Application No. 2003-136710, filed on May 15, 2003, the entire contents of which are hereby incorporated by reference.

BACKGROUND OF THE INVENTION

The present invention relates to a novel arylamine compound and an organic electroluminescent device using the same, specifically to an organic electroluminescent device which has a high luminance, a high heat resistance and a long life and which is excellent in a hole transporting property and has a high luminous efficiency and a novel arylamine compound which realizes the same.

RELATED ART

An organic electroluminescent (EL) device using an organic substance is used as a light source for a plane emitter for a wall-mounted television set and a backlight for a display, and it has actively been developed. An electroluminescent phenomenon of organic materials was observed on anthracene single crystal by Pope et al. in 1963 (J. Chem. Phys. 38 (1963) 2042), and Helfinch and Schneider succeeded in observing relatively strong injection type EL by using a solution electrode system having a good injection efficiency (Phys. Rev. Lett. 14 (1965) 229). As reported since then, it has been researched to form organic luminous substances from conjugate organic host substances and conjugate organic activators having condensed benzene rings. Shown as the examples of the organic host substances were naphthalene, anthracene, phenanthrene, tetracene, pyrene, benzopyrene, chrysene, picene, carbazole, fluorene, biphenyl, terphenyl, triphenylene oxide, dihalobiphenyl, trans-stilbene and 1,4-diphenylbutadiene, and anthracene, tetracene and pentacene were given as the examples of the activators. However, all of the above organic luminous substances were present in the form of a single layer having a thickness exceeding 1 μm, and a high electric field was required for luminescence. Accordingly, research of thin film devices by a vacuum vapor deposition method was promoted (for example, Thin Solid Films 94 (1982) 171). However, though a reduction in a film thickness was effective for a reduction in a driving voltage, it did not come to obtain a device of a practical use level having a high luminance. Then, Tang et al. devised an EL device prepared by laminating two very thin films (a hole transporting layer and a luminescent layer) between an anode and a cathode by vacuum vapor deposition to realize a high luminance at a low driving voltage (Appl. Phys. Lett. 51 (1987) 913 or U.S. Pat. No. 4,356,429). Then, developments of organic compounds used for a hole transporting layer and a luminescent layer were promoted for ten and several years, and as a result thereof, an organic EL device was started being put into practical use in display parts of car stereos and portable telephones.

However, durability of the luminance against deterioration with the passage of time in use for long time is not satisfactory in terms of actual use and required to be further improved. In particular, when considering application thereof to full color displays, it is required to the respective colors of R, G and B to achieve a half life of several thousand hours at a high luminance of 300 cd/m² or more. It is particularly difficult in phosphorescent type luminescence to achieve this. Energy gap in a luminescent layer is as large as 3.0 eV or more, and large energy barrier is present between a hole transporting layer and a luminescent layer in injecting a hole, so that a field intensity applied to the interface is large, and a hole can not stably be injected in a conventional hole transporting layer. Accordingly, improvement thereof has been required. Further, on the assumption that an organic EL device is mounted on a car, a preserving performance thereof at a high temperature is required, but it is pointed out that it has a problem on a preserving performance at a high temperature of 100° C. or higher. Also in this case, it is pointed out that a glass transition temperature is low in a conventional hole transporting layer, and it has been tried to cope therewith only by improving the glass transition temperature to 100° C. or higher, but it is unsatisfactory, and the good preserving performance at a high temperature has not yet been realized.

Various inventions have been made in order to solve the problems described above, and a luminescent device in which a compound represented by the following Formula (A) is used as a hole transporting material is disclosed in, for example, Japanese Patent Application Laid-Open No. 25473/1993:

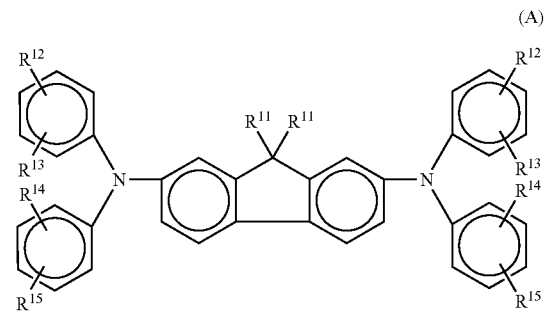

(A)

wherein $R^{11}$ represents an alkyl group or an aralkyl group, and $R^{12}$ to $R^{15}$ represent a hydrogen atom, an alkyl group, an alkoxy group or a halogen atom.

However, the above compound had a glass transition temperature of 100° C. or lower, and a device prepared by using the same had a short life and was short of a heat resistance, so that it could not be put into practical use. Further, known is a compound obtained by changing $R^{12}$ to $R^{15}$ to aryl groups in order to improve the above matter, but it is scarcely soluble and therefore hard to be highly purified, so that a problem has been involved in using it as a material for a long life device.

Further, a luminescent device in which a compound represented by the following Formula (B) is used as a hole transporting material is disclosed in Japanese Patent Application Laid-Open No. 288783/1999:

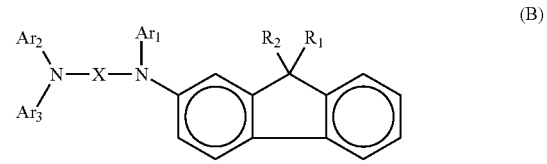

(B)

wherein Ar₁ to Ar₃ each represent a substituted or non-substituted aryl group, and Ar₂ and Ar₃ may form a nitrogen-containing heterocycle together with a nitrogen atom to which they are bonded; R₁ and R₂ each represent a hydrogen atom, a linear, branched or cyclic alkyl group, a substituted or non-substituted aryl group or a substituted or non-substituted aralkyl group; Z₁ and Z₂ each represent a hydrogen atom, a halogen atom, a linear, branched or cyclic alkyl group, a linear, branched or cyclic alkoxy group or a substituted or non-substituted aryl group; and X represents a substituted or non-substituted arylene group.

A fluorene group is introduced into the above compounds, but the glass transition temperatures are still low and have been required to be improved. Further, the fluorene groups present at the ends thereof have a high flatness and therefore cause interactions (exiplex, charge-transfer complex and the like) with compounds in the other layers in constituting a laminate, so that there used to be involved therein the problem that a luminescent efficiency of the devices is reduced.

DISCLOSURE OF THE INVENTION

The present invention has been made in order to solve the problems described above, and an object thereof is to provide an organic EL device which has a high luminance, a high heat resistance and a long life and which is excellent in a hole transporting property and has a high luminous efficiency and a novel arylamine compound which realizes the same.

Intensive researches repeated by the present inventors in order to achieve the object described above have resulted in finding that use of an arylamine compound of a specific structure having at least one spiro bond provides an organic EL device which has a high heat resistance and a long life because of a high glass transition temperature and which is excellent in a hole transporting property and has a high luminous efficiency because of increased steric hindrance and less liability of association due to a flatness of molecules which is reduced by containing the specific spiro bond, and thus they have come to complete the present invention.

That is, the present invention provides an arylamine compound represented by the following Formula (1):

wherein X is a substituted or non-substituted aromatic hydrocarbon group having 6 to 40 carbon atoms or a substituted or non-substituted heterocyclic group having 5 to 40 carbon atoms; $Ar^1$, $Ar^2$, $Ar^3$ and $Ar^4$ each are independently a substituted or non-substituted aryl group having 6 to 40 carbon atoms or a substituted or non-substituted heterocyclic group having 5 to 40 carbon atoms; provided that at least one of $Ar^1$, $Ar^2$, $Ar^3$ and $Ar^4$ is a group represented by the following Formula (2); $Ar^1$, $Ar^2$, $Ar^3$ and $Ar^4$ may be the same as or different from each other, and they may be combined with adjacent ones to form a saturated or unsaturated ring; and p is an integer of 0 to 2:

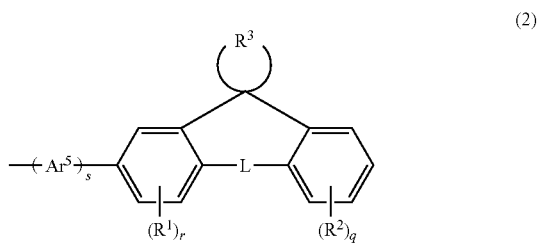

wherein $R^1$ and $R^2$ each are independently a hydrogen atom, a substituted or non-substituted amino group, a substituted or non-substituted alkyl group having 1 to 50 carbon atoms, a substituted or non-substituted aryl group having 6 to 40 carbon atoms or a substituted or non-substituted heterocyclic group having 5 to 40 carbon atoms; $R^3$ represents an atomic group which forms a cyclic structure; $Ar^5$ is a single bond or a divalent group comprising a substituted or non-substituted aromatic hydrocarbon group having 6 to 40 carbon atoms or a substituted or non-substituted heterocyclic group having 5 to 40 carbon atoms; L is a single bond, —O—, —S—, —NR⁴— or —CR⁵R⁶— ($R^4$, $R^5$ and $R^6$ each are independently a substituted or non-substituted alkyl group having 1 to 50 carbon atoms or a substituted or non-substituted aryl group having 6 to 40 carbon atoms); s, q and r each are an integer of 0 to 2; and $R^1$ and $R^2$ may be combined with each other to form a ring.

Further, the present invention provides an organic EL device in which an organic compound layer comprising one layer or plural layers including at least a luminescent layer is interposed between a cathode and an anode, wherein at least one of the above organic compound layers contains the arylamine derivative described above; an organic EL device in which an organic compound layer comprising one layer or plural layers including at least a luminescent layer is interposed between a cathode and an anode, wherein at least one of the above organic compound layers contains the arylamine derivative described above and a luminescent material; and an organic EL device in which an organic compound layer comprising one layer or plural layers including at least a luminescent layer is interposed between a cathode and an anode, wherein the above organic compound layer is prepared by laminating a hole transporting layer containing the arylamine derivative described above and a luminescent layer comprising a phosphorescence-emitting metal complex and a host material.

BEST MODE FOR CARRYING OUT THE INVENTION

The arylamine compound of the present invention is represented by the following Formula (1):

In Formula (1), X is a substituted or non-substituted aromatic hydrocarbon group having 6 to 40 carbon atoms or a substituted or non-substituted heterocyclic group having 5 to 40 carbon atoms.

The examples of the aromatic hydrocarbon group represented by X include monovalent, divalent or trivalent residues of benzene, biphenyl, terphenyl, naphthalene, fluorene, pyrene, spirobifluorene and stilbene, and benzene and condensed aromatic ring residues of naphthalene, fluorene and pyrene are preferred.

The examples of the heterocyclic group represented by X include monovalent, divalent or trivalent residues of carbazole, dibenzofurane, dibenzothiophene, fluorenone, oxazole, oxadiazole, thiadiazole and benzimidazole, and the residues of carbazole and benzimidazole are preferred.

The substituents for the above groups include halogen atoms such as a fluorine atom, a chlorine atom, a bromine atom and an iodine atom, alkyl groups such as methyl, ethyl, n-propyl and iso-propyl, alkoxy groups such as methoxy, ethoxy and phenoxy, aralkyl groups such as benzyl, phenethyl and propylphenyl, a nitro group, a cyano group, substituted amino groups such as dimethylamino, dibenzylamino, diphenylamino and morpholino, aryl groups such as phenyl, toluyl, biphenyl, naphthyl, anthryl and pyrenyl and heterocyclic groups such as pyridyl, thienyl, furyl, quinolyl and carbazolyl.

In Formula (1), $Ar^1$, $Ar^2$, $Ar^3$ and $Ar^4$ each are independently a substituted or non-substituted aryl group having 6 to 40 carbon atoms or a substituted or non-substituted heterocyclic group having 5 to 40 carbon atoms.

Provided that at least one of $Ar^1$, $Ar^2$, $Ar^3$ and $Ar^4$ is a group represented by the following Formula (2), and two to four of them are preferably the group represented by the following Formula (2).

Further, $Ar^1$, $Ar^2$, $Ar^3$ and $Ar^4$ may be the same as or different from each other, and they may be combined with adjacent ones to form a saturated or unsaturated ring.

The examples of the aryl group represented by $Ar^1$ to $Ar^4$ include phenyl, biphenyl, terphenyl, naphthyl, fluorenyl, pyrenyl, spirobifluorenyl and stilbenyl, and phenyl and condensed polycyclic aromatic groups such as naphthyl, fluorenyl and pyrenyl are preferred.

The examples of the heterocyclic group represented by $Ar^1$ to $Ar^4$ include carbazolyl, dibenzofuranyl, dibenzothiophenyl, fluorenonyl, oxazolyl, oxadiazolyl, thiadiazole and benzimidazole, and carbazolyl and benzimidazole are preferred.

The substituents for the above groups include the same ones as explained in X described above.

In the arylamine compound of the present invention, at least two of $Ar^1$ to $Ar^4$ in Formula (1) are preferably aromatic hydrocarbons having 10 or more carbon atoms, and further preferably, at least two of $Ar^1$ to $Ar^4$ are substituted or non-substituted biphenyl or at least one of $Ar^1$ to $Ar^4$ is a group substituted with a diarylamino group.

The term p is an integer of 0 to 2.

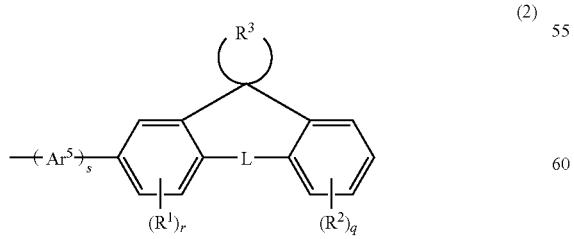

(2)

In Formula (2), $R^1$ and $R^2$ each are independently a hydrogen atom, a substituted or non-substituted amino group, a substituted or non-substituted alkyl group having 1 to 50 carbon atoms, a substituted or non-substituted aryl group having 6 to 40 carbon atoms or a substituted or non-substituted heterocyclic group having 5 to 40 carbon atoms.

The substituted or non-substituted amino group represented by $R^1$ and $R^2$ includes phenylamino, dimethylamino, benzylamino, diphenylamino and morpholino.

The alkyl group represented by $R^1$ and $R^2$ includes methyl, ethyl, n-propyl, iso-propyl, n-butyl, s-butyl and t-butyl.

The aryl group and the heterocyclic group represented by $R^1$ and $R^2$ include the same ones as explained in $Ar^1$ to $Ar^4$ described above.

The substituents for the above groups include the same ones as explained in X described above.

$R^1$ and $R^2$ may be combined with each other to form a ring.

$R^3$ represents an atomic group which forms a cyclic structure and includes, for example, alkylene groups such as an ethylene group, a propylene group, a n-butylene group, a n-pentylene group and a n-hexylene group and groups in which at least one of the above alkylene groups is substituted with a nitrogen atom or an oxygen atom to form a heterocycle. They may have substituents. Further, the substituents may be combined with each other to form an unsaturated ring. The substituents include the same ones as explained in X described above.

The specific examples of the group represented by Formula (2) include the following ones:

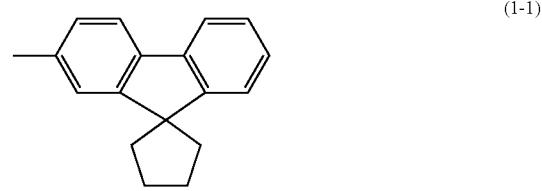

(1-1)

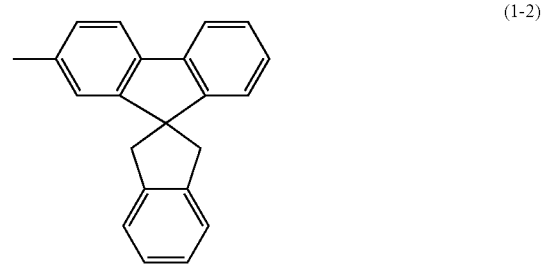

(1-2)

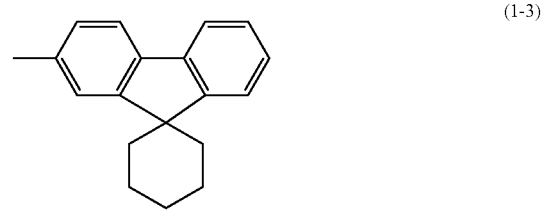

(1-3)

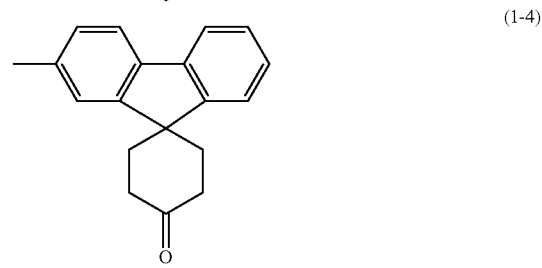

(1-4)

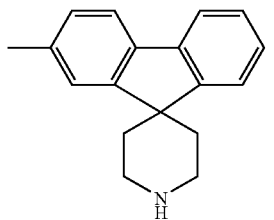 (1-5)

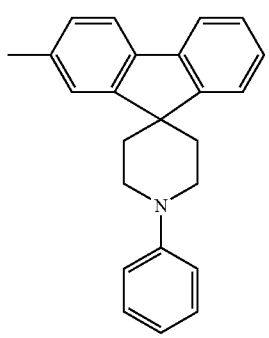 (1-6)

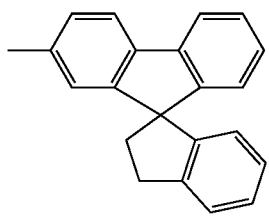 (1-7)

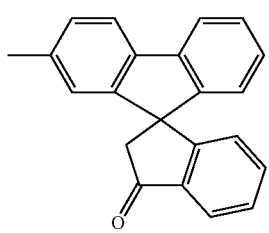 (1-8)

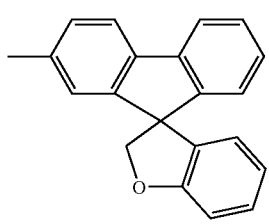 (1-9)

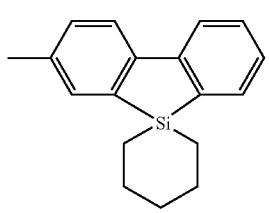 (1-10)

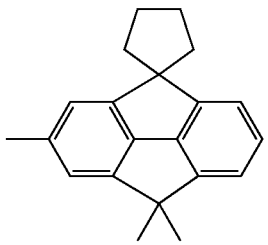 (1-11)

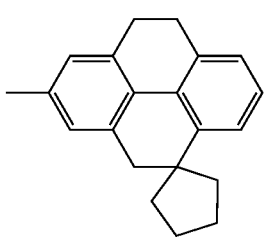 (1-12)

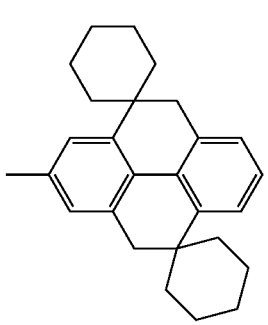 (1-13)

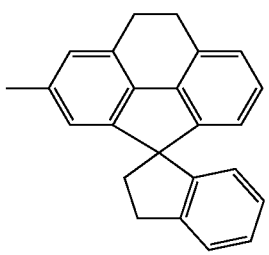 (1-14)

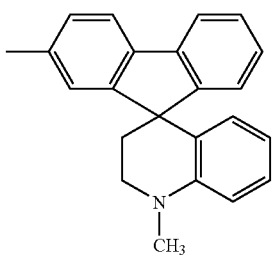 (1-15)

In Formula (2), $Ar^5$ is a single bond or a divalent group comprising a substituted or non-substituted aromatic hydrocarbon group having 6 to 40 carbon atoms or a substituted or non-substituted heterocyclic group having 5 to 40 carbon atoms.

The examples of the aromatic hydrocarbon group represented by $Ar^5$ include divalent residues of benzene, biphenyl, terphenyl, naphthalene, fluorene, pyrene spirofluorene and stilbene.

The examples of the heterocyclic group represented by $Ar^5$ include divalent residues of carbazole, dibenzofurane, dibenzothiophene, fluorenone, oxazole, oxadiazole, thiadiazole and benzimidazole.

The substituents for the above groups include the same ones as explained in X described above.

In Formula (2), L is a single bond, —O—, —S—, —$NR^4$— or —$CR^5R^6$— ($R^4$, $R^5$ and $R^6$ each are independently a substituted or non-substituted alkyl group having 1 to 50 carbon atoms or a substituted or non-substituted aryl group having 6 to 40 carbon atoms).

The specific examples of the alkyl group and the aryl group represented by $R^4$, $R^5$ and $R^6$ and the substituents therefor include the same ones as explained in $R^1$ and $R^2$ described above.

The terms s, q and r each are an integer of 0 to 2.

The arylamine compound of the present invention represented by Formula (1) is obtained, for example, by reacting a corresponding iodo compound with a corresponding amine compound. The reaction is preferably carried out under the presence of a catalyst, and the catalyst includes a metal catalyst, for example, a copper catalyst.

The example of a production process for the arylamine compound of the present invention includes the following route. That is, an iodo compound represented by the following Formula (3):

(wherein X is the same as described above) is reacted with an amine compound represented by the following Formula (4) or Formula (4) and Formula (5):

(wherein $Ar^1$ to $Ar^4$ are the same as described above) to obtain the arylamine compound represented by Formula (1).

The specific examples of the arylamine compound of the present invention represented by Formula (1) shall be shown below, but they shall not be restricted to these compounds shown as the examples.

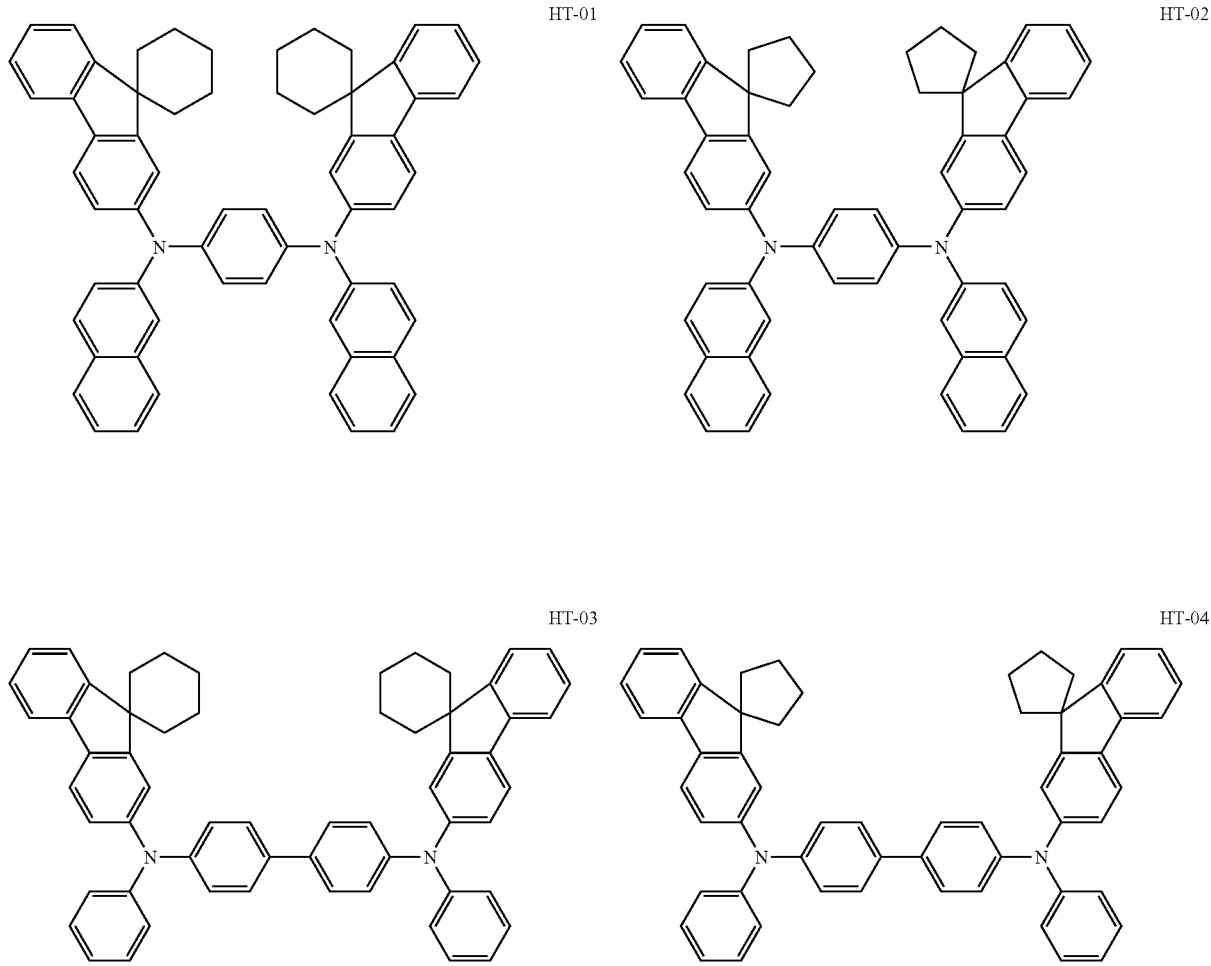

-continued
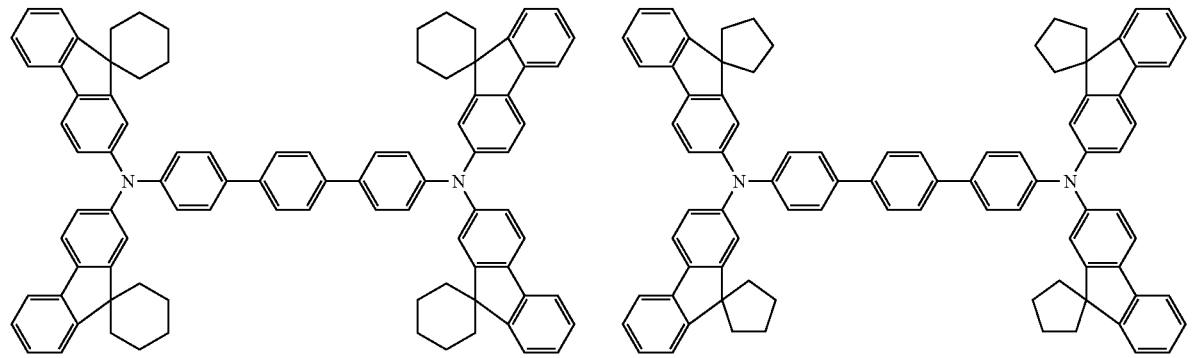
HT-05
HT-06
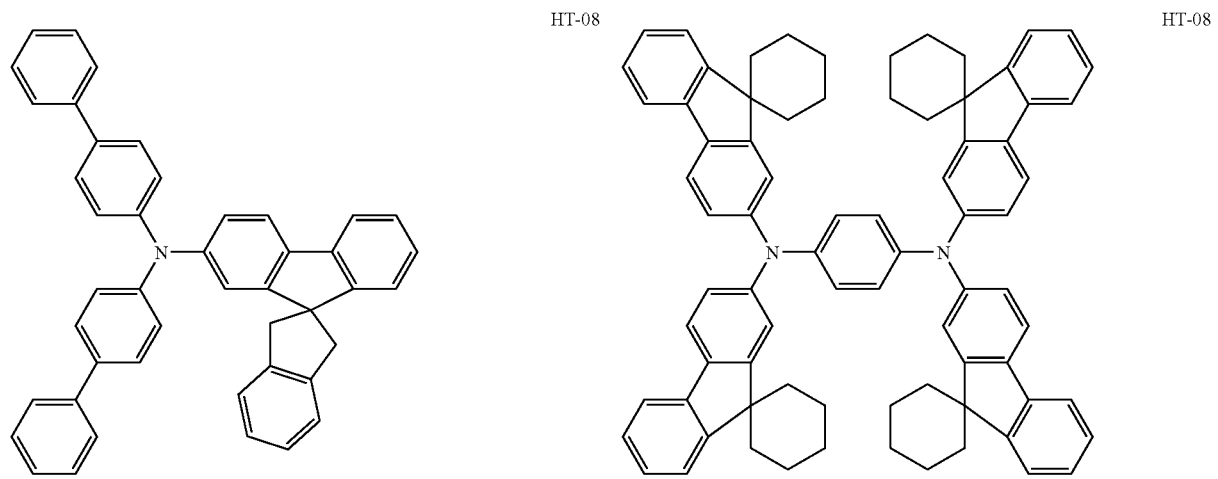
HT-08
HT-08
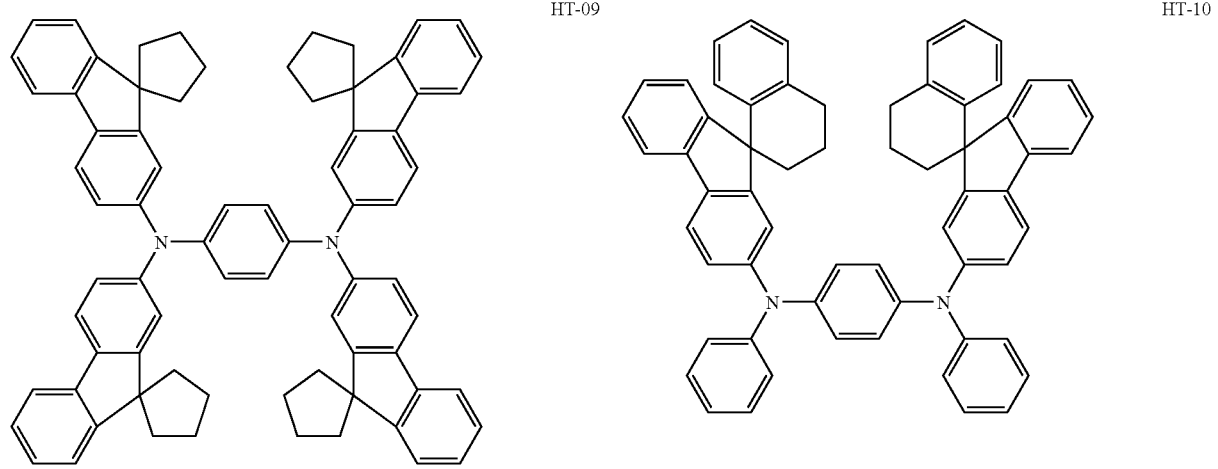
HT-09
HT-10

-continued
HT-11
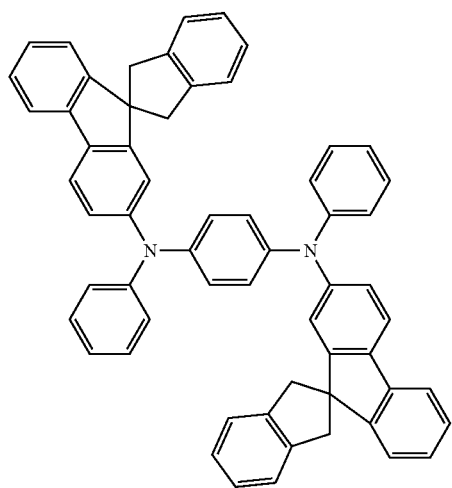
HT-12
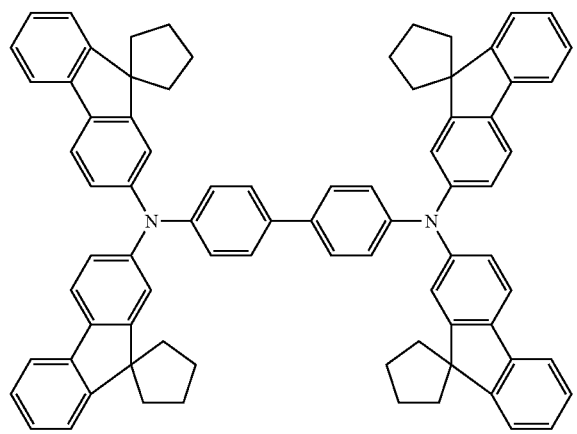
HT-13
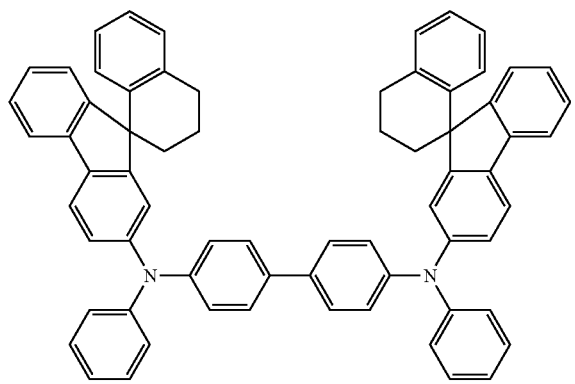
HT-14
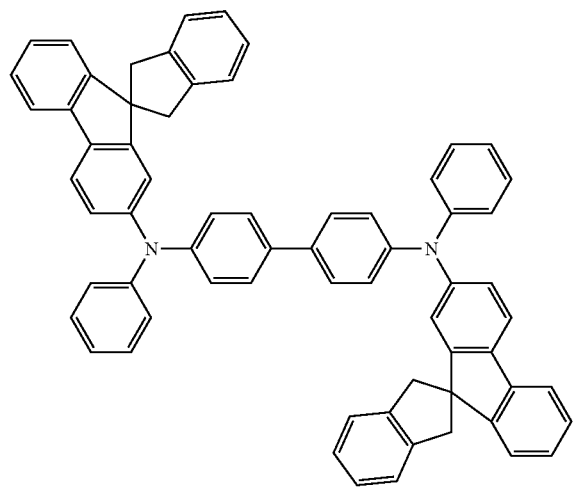
HT-15
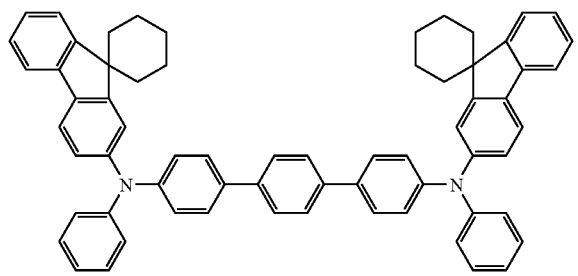
HT-16
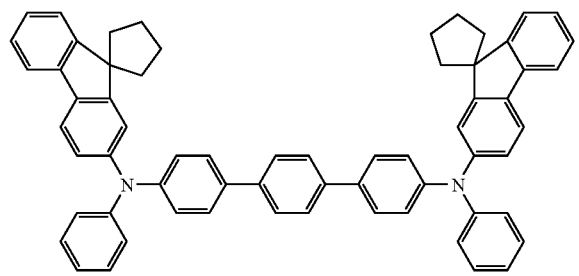

-continued
HT-17
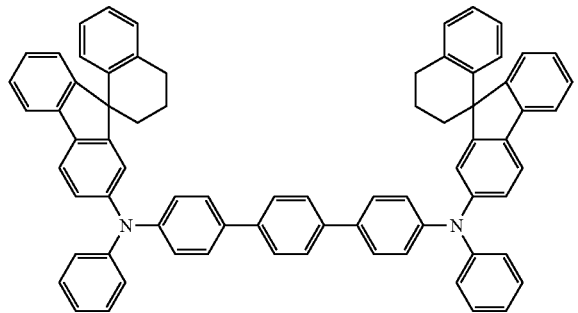
HT-18
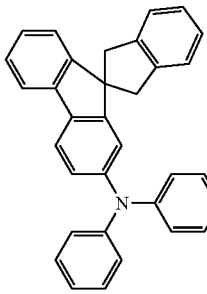
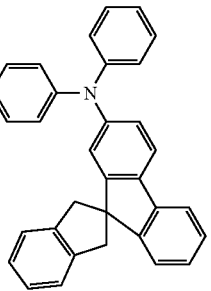
HT-19
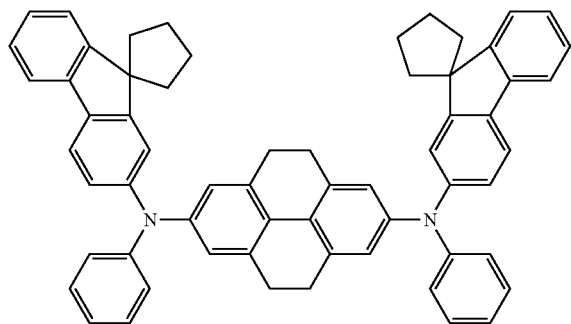
HT-20
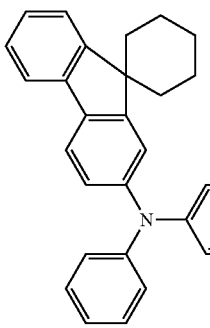
HT-21
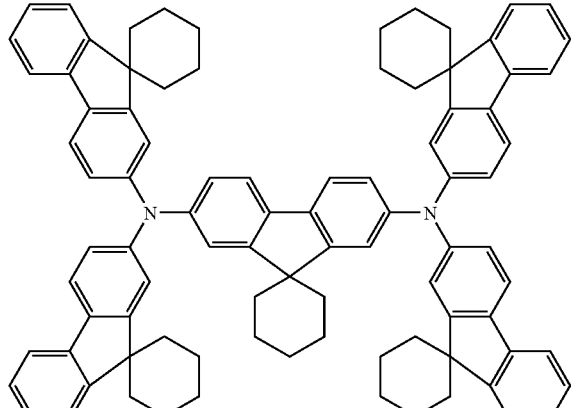
HT-22
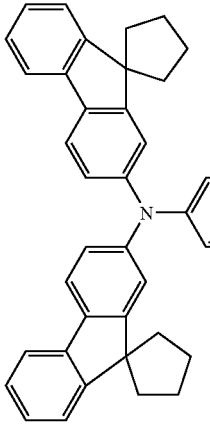
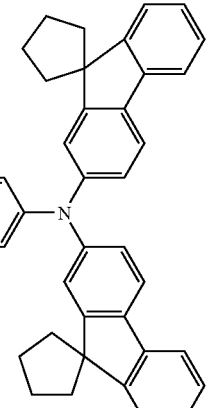
HT-23
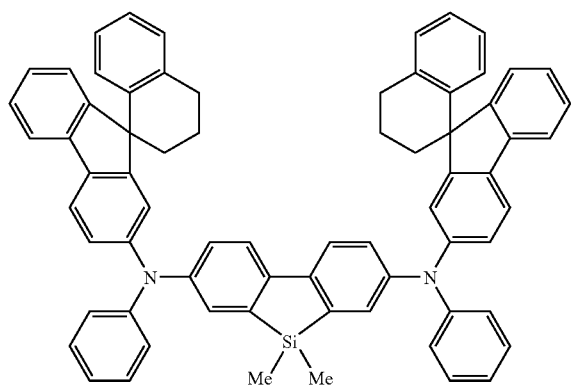
HT-24
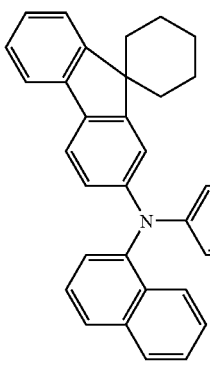

-continued
HT-25
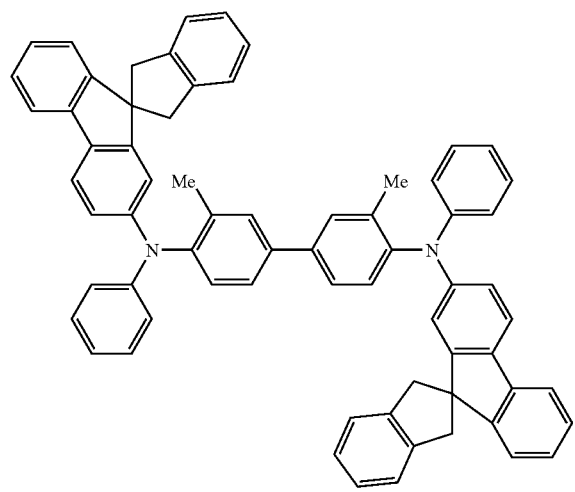
HT-26
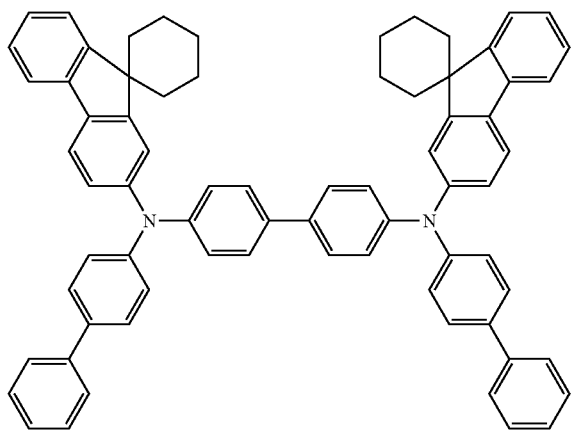
HT-27
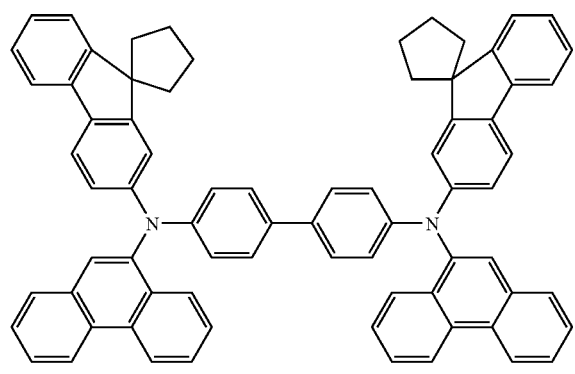
HT-28
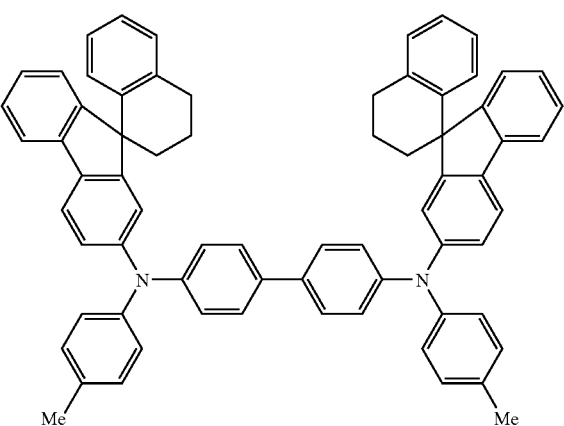
HT-29
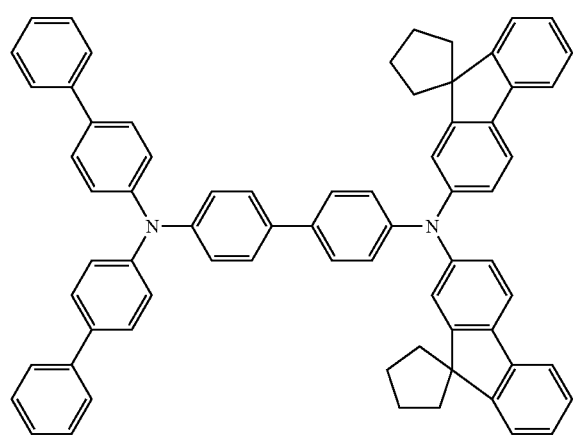
HT-30
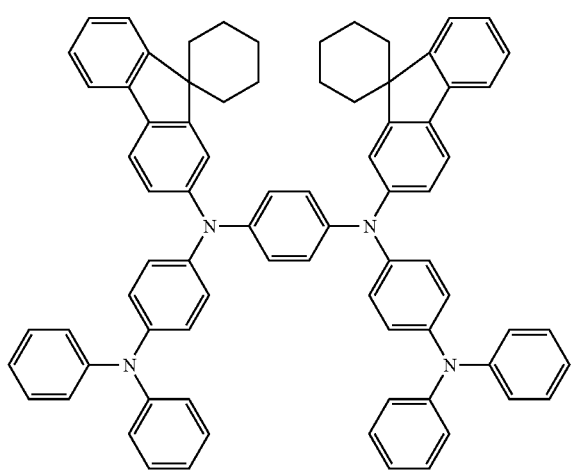

-continued
HT-31
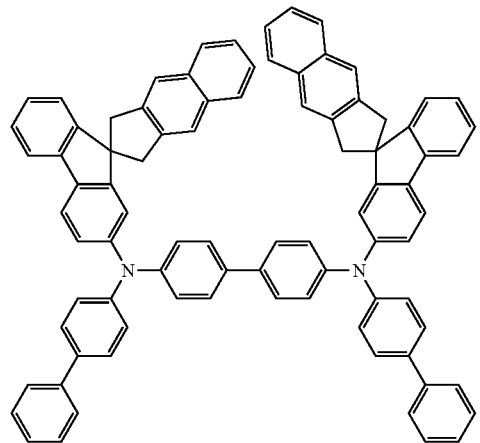
HT-32
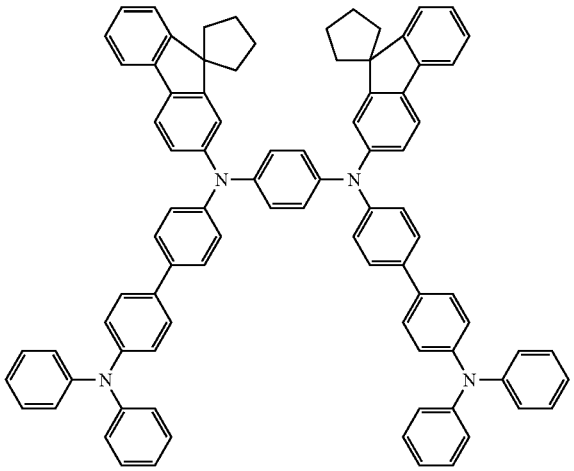
HT-33
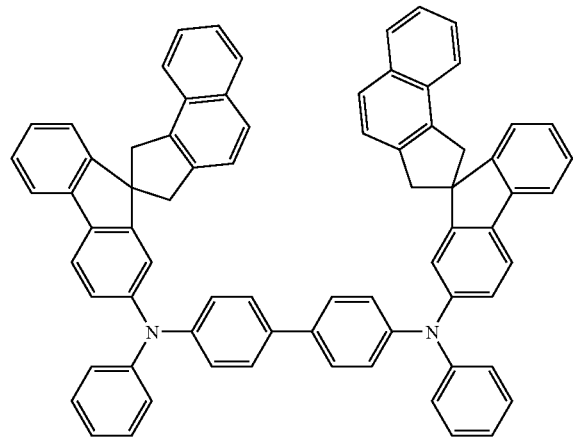
HT-34
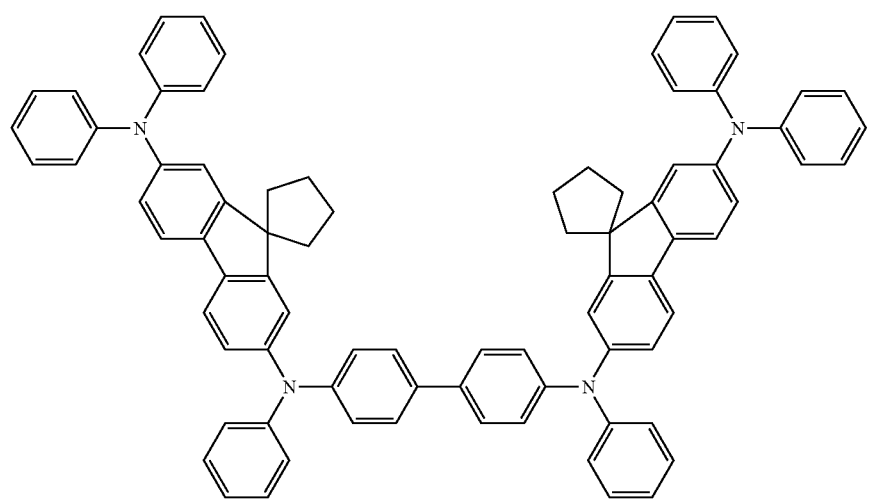

-continued
HT-35
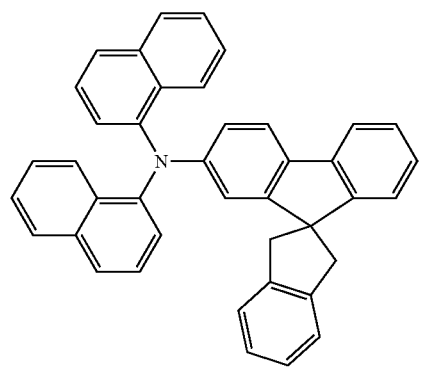
HT-36
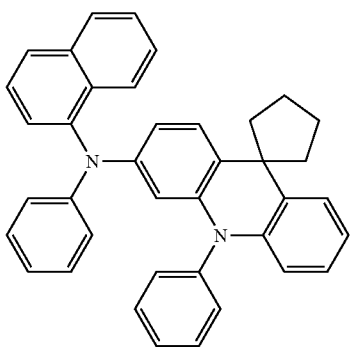
HT-37
HT-38
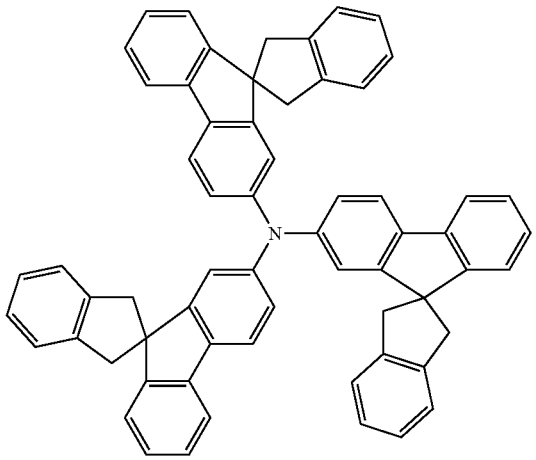
HT-39
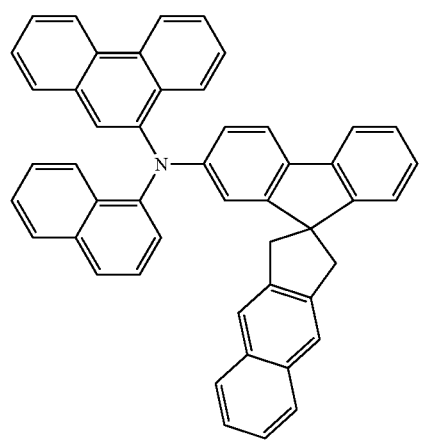
HT-40
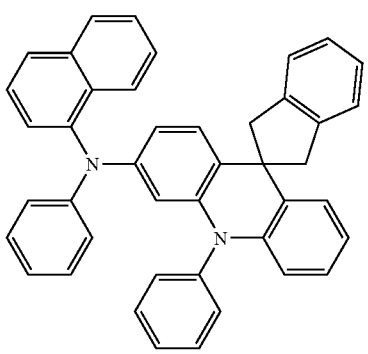

-continued
HT-41
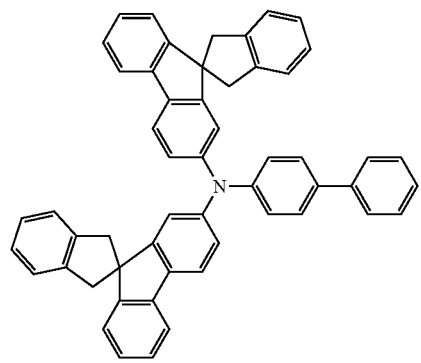
HT-42
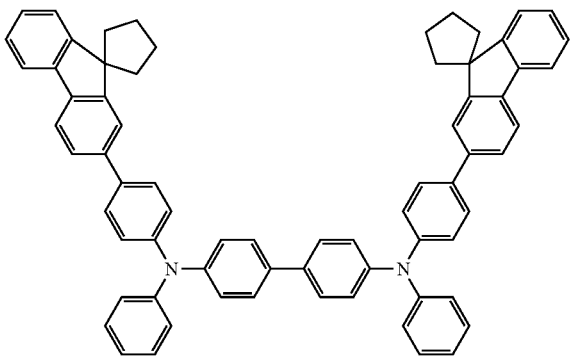
HT-43
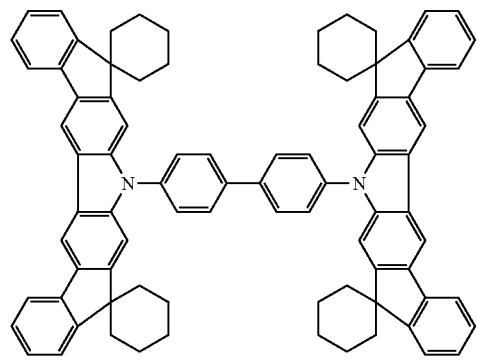
HT-44
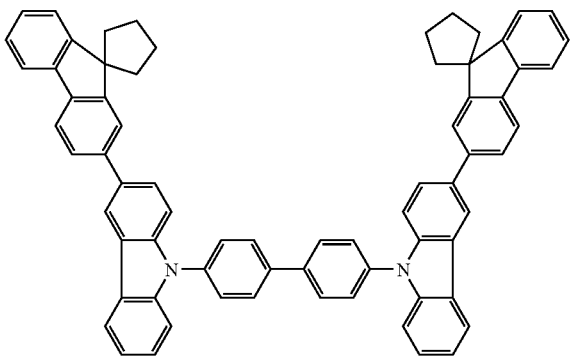
HT-45
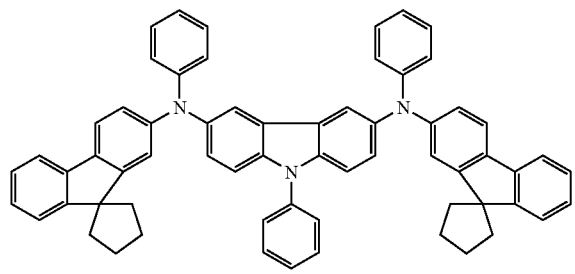
HT-46
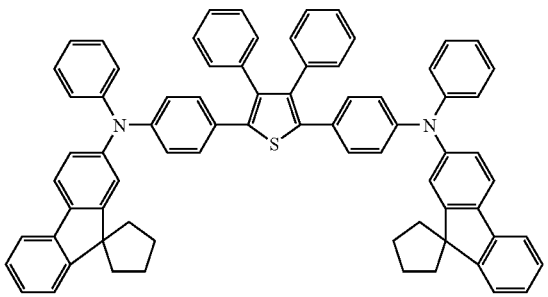
HT-47
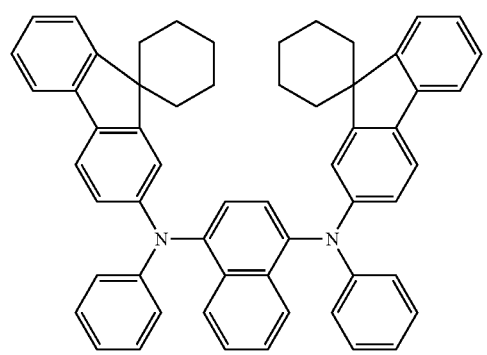
HT-48
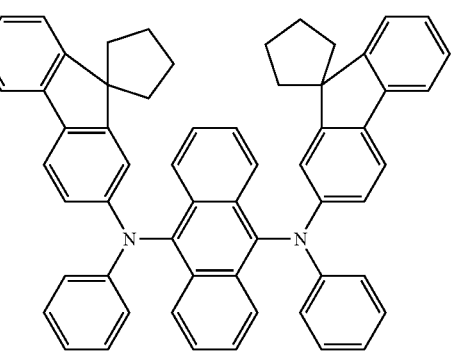

HT-49

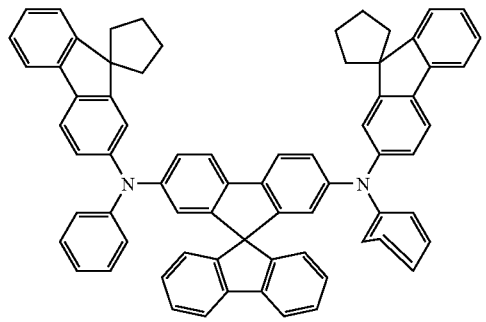

HT-50

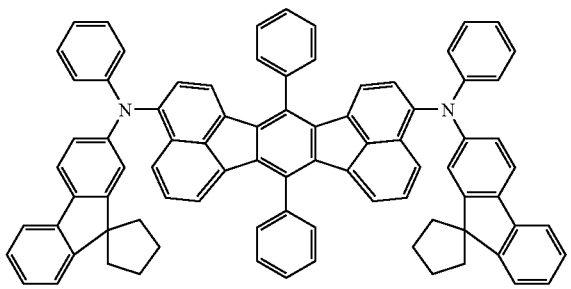

The arylamine compound of the present invention is useful as a material for an organic EL device, and it is particularly preferably used as a hole transporting material.

The device structure of the organic EL device of the present invention shall be explained below.

In the organic EL device of the present invention in which an organic compound layer comprising a single layer or plural layers including at least a luminescent layer is interposed between a cathode and an anode, at least one layer of the above organic compound layers contains the arylamine compound of the present invention described above.

The organic EL device is improved in a luminance, a heat resistance, a life and a luminous efficiency by adding the arylamine compound of the present invention to at least one layer of the organic compound layers because the arylamine compound is excellent in a hole transporting property, and a hole can stably be injected; a glass transition temperature is high; a flatness of molecules is reduced due to a spiro bond contained therein, so that steric hindrance is increased; it is less liable to interact with the luminescent material, and non-radiation transition caused by the interaction can be avoided.

The organic EL device of the present invention is a device in which an organic compound layer comprising a single layer or plural layers is formed between an anode and a cathode. In the case of the single layer type, a luminescent layer is provided between an anode and a cathode. The luminescent layer contains the luminescent material, and in addition thereto, it may contain a hole injecting material or an electron injecting material in order to transport a hole injected from the anode or an electron injected from the cathode to the luminescent material. The luminescent material has a very high fluorescent quantum efficiency and a high hole transporting ability and electron transporting ability in combination, and an even thin film is preferably formed. The organic EL element of the multilayer type includes (anode/hole injecting layer (hole transporting layer)/luminescent layer/cathode), (anode/luminescent layer/electron injecting layer/cathode) and (anode/hole injecting layer (hole transporting layer)/luminescent layer/electron injecting layer/cathode).

In the present invention, the luminescent layer described above preferably contains the arylamine compound of the present invention. Further, the organic compound layer described above preferably has a hole transporting layer, and the above hole transporting layer preferably contains the arylamine compound of the present invention.

A preferred use method of the arylamine compound of the present invention includes adding it to any layer of the luminescent layer, the electron injecting layer and the hole transporting layer in a concentration of 0.5 to 100% by weight, more preferably 50 to 100% by weight. The organic EL element can be prevented from a reduction in a luminance and a life due to quenching by assuming a multilayer structure. The luminescent material, other doping materials, a hole injecting material and an electron injecting material can be used, if necessary, in combination. The other doping materials make it possible to obtain a rise in the light emitting luminance and the luminous efficiency and luminance of a red color and a white color. The hole injecting layer, the luminescent layer and the electron injecting layer each may be formed in a layer structure of two or more layers. In such case, as long as the hole injecting layer is concerned, a layer into which a hole is injected from an electrode is called a hole injecting layer, and a layer which receives a hole from the hole injecting layer and transports it to a luminescent layer is called a hole transporting layer. Similarly, as long as the electron injecting layer is concerned, a layer into which an electron is injected from an electrode is called an electron injecting layer, and a layer which receives an electron from the electron injecting layer and transports it to the luminescent layer is called an electron transporting layer. The above respective layers are selected and used according to respective factors such as an energy level of the materials, a heat resistance and an adhesion to the organic compound layer or the metal electrode.

The organic EL device of the present invention preferably contains the arylamine compound of the present invention and the luminescent material in at least one layer of the organic compound layers described above.

The luminescent material which can be used in the organic compound layer together with the arylamine compound of the present invention includes condensed polycyclic aromatic compounds, and they include, for example, anthracene, naphthalene, phenanthrene, pyrene, tetracene, pentacene, coronene, chrysene, fluorescein, perylene, rubrene and derivatives thereof. Further, they include phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, quinoline metal complexes, aminoquinoline metal complexes, benzoquinoline metal complexes, imine, diphenylethylene, vinylanthracene, diaminocarbazole, pyran, thiopyran, polymethine, merocyanine, imidazole chelated oxynoid compounds, quinacridone, rubrene, stilbene base derivatives and fluorescent coloring matters. However, it shall no be restricted to them.

Further, in the organic EL device of the present invention, the organic compound layer described above is preferably prepared by laminating a hole transporting layer containing the arylamine derivative of the present invention and a luminescent layer comprising a phosphorescence-emitting metal complex and a host material.

The phosphorescence-emitting metal complex includes:

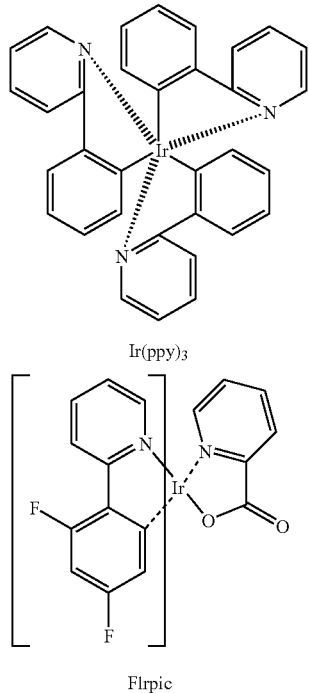

Ir(ppy)₃

FIrpic but shall not be restricted to them.

The host material described above includes condensed polycyclic aromatic compounds, and they include, for example, anthracene, naphthalene, phenanthrene, pyrene, tetracene, pentacene, coronene, chrysene, fluorescein, perylene, rubrene and derivatives thereof. Further, they include phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, quinoline metal complexes, aminoquinoline metal complexes, benzoquinoline metal complexes, imine, diphenylethylene, vinylanthracene, diaminocarbazole, pyran, thiopyran, polymethine, merocyanine, imidazole chelated oxynoid compounds, quinacridone, rubrene, stilbene base derivatives and fluorescent coloring matters. However, it shall not be restricted to them.

Further, publicly known luminescent materials, doping materials, hole injection materials and electron injection materials in addition to the arylamine compound of the present invention can be used, if necessary, in the luminescent layer described above.

The luminescent materials described above include those described above.

Capable of being used as the doping materials described above are publicly known fluorescent coloring matters such as perylene derivatives, rubrene derivatives, coumarin derivatives, dicyanomethylenepyran derivatives, stilbene derivatives, tristyrylarylene derivatives and distyrylarylene derivatives. Among them, the distyrylarylene derivatives can be given as the preferred fluorescent coloring matters. Further preferably, styrylamine compounds such as arylamino-substituted distyrylarylene derivatives can be given. Also, arylamine compounds can preferably be used as well for the dopant.

Preferred as the hole injecting materials described above are compounds which are provided with ability to transport holes and have an effect of injecting holes from an anode and an excellent effect of injecting holes into a luminescent layer or a luminescent material and which prevent excitons formed in the luminescent layer from transferring to an electron injecting layer or an electron injecting material and are excellent in a thin film-forming ability. To be specific, they include phthalocyanine derivatives, naphthalocyanine derivatives, porphyrin derivatives, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine and derivatives thereof and high molecular materials such as polyvinylcarbazole, polysilane and conductive polymers, but they shall not be restricted thereto.

Among the above hole injecting materials, more effective hole injection materials are aromatic tertiary amine derivatives or phthalocyanine derivatives. The specific examples of the aromatic tertiary amine derivatives are triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N, N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-triaminophenyl)-4-phenyl-cyclohexane and oligomers or polymers having aromatic tertiary amine skeletons thereof, but they shall not be restricted thereto. The specific examples of the phthalocyanine (Pc) derivatives include phthalocyanine derivatives such as H₂Pc, CuPc, CoPc, NiPc, ZnPc, PdPc, FePc, MnPc, ClAlPc, ClGaPc, ClInPc, ClSnPc, Cl₂SnPc, (HO)AlPc, (HO)GaPc, VoPc, TiOPc, MoOPc and GaPc-O-GaPc and naphthalocyanine derivatives, but they shall not be restricted thereto.

Preferred as the electron injecting materials described above are compounds which are provided with ability to transport electrons and have an effect of injecting electrons from a cathode and an excellent effect of injecting electrons into a luminescent layer or a luminescent material and which prevent excitons formed in the luminescent layer from transferring to a hole injecting layer and are excellent in a thin film-forming ability. To be specific, they include fluorenone, anthraquinodimethane, diphenoquinone, thiopyran dioxide, oxazole, oxadiazole, triazole, imidazole, perylenetetracarboxylic acid, fluorenilidenemethane, anthraquinodimethane, anthrone and derivatives thereof, but they shall not be restricted thereto. Further, the charge injecting property can be raised by adding an electron receiving substance to the hole injecting material and adding an electron donating substance to the electron injecting material.

Among the above hole injecting materials, more effective electron injecting materials are metal complex compounds or nitrogen-containing five-membered derivatives. The specific examples of the metal complex compounds include 8-hydroxyquinolinate lithium, bis(8-hydroxyquinolinate) zinc, bis(8-hydroxyquinolinate) copper, bis(8-hydroxyquinolinate) manganese, tris(8-hydroxyquinolinate) aluminum, tris (2-methyl-8-hydroxyquinolinate) aluminum, tris(8-hydroxyquinolinate) gallium, bis(10-hydroxybenzo[h]quinolinate) beryllium, bis(10-hydroxybenzo[h]quinolinate) zinc, bis(2-methyl-8-quinolinate) chlorogallium, bis(2-methyl-8-quinolinate) (o-crezolate) gallium, bis(2-methyl-8-quinolinate) (o-naphtholate) aluminum, bis(2-methyl-8-quinolinate) (1-naphtholate) aluminum and bis(2-methyl-8-quinolinate) (2-naphtholate) gallium, but they shall not be restricted thereto.

The nitrogen-containing five-membered derivatives are preferably oxazole, thiazole, oxadiazole, thiadiazole and triazole derivatives. To be specific, they include 2,5-bis(1-phenyl)-1,3,4-oxazole, dimethyl POPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole and 1,4-bis[2-(5-phenyltriazolyl)]benzene, but they shall not be restricted thereto.

In the present invention, an inorganic compound layer may be provided between the luminescent layer and the electrode in order to improve the charge injecting property. Such inorganic compound includes alkaline metal compounds (fluorides, oxides and the like) and alkaline earth metal compounds, and to be specific, it includes LiF, $Li_2O$, RaO, SrO, $BaF_2$ and $SrF_2$.

The conductive material used for the anode in the organic EL device of the present invention is suitably a material having a work function of larger than 4 eV, and used therefor are carbon, aluminum, vanadium, iron, cobalt, nickel, tungsten, silver, gold, platinum, palladium and alloys thereof, metal oxides such as tin oxide and indium oxide which are used for an ITO substrate and an NESA substrate and organic conductive resins such as polythiophene and polypyrrole.

The conductive material used for the cathode in the organic EL device of the present invention is suitably a material having a work function of smaller than 4 eV, and used therefore are magnesium, calcium, tin, lead, titanium, yttrium, lithium, ruthenium, manganese, aluminum and alloys thereof, but it shall not be restricted to them. The representative examples of the alloys include, for example, magnesium/silver, magnesium/indium and lithium/aluminum. A proportion of the alloys is controlled according to a temperature of the vapor deposition source, the atmosphere and the vacuum degree, and the suitable proportion is selected. The anode and the cathode may be formed, if necessary, in a layer structure of two or more layers.

In the organic EL device of the present invention, it is preferred that at least one surface thereof is sufficiently transparent in a luminescent wavelength area of the device in order to efficiently emit light. Further, the substrate is preferably transparent as well. A transparent electrode is set up by a method such as vapor deposition and sputtering using the conductive materials described above so that prescribed transparency is secured. The electrode on the luminescent face is preferably controlled to a light transmittance of 10% or more. The substrate shall not be restricted as long as it has mechanical and thermal strengths and is transparent, and it includes a glass substrate and a transparent resin film. The transparent resin film includes polyethylene, an ethylene-vinyl acetate copolymer, an ethylene-vinyl alcohol copolymer, polypropylene, polystyrene, polymethyl methacrylate, polyvinyl chloride, polyvinyl alcohol, polyvinyl butyral, nylon, polyether ether ketone, polysulfone, polyether sulfone, a tetrafluoroethylene-perfluoroalkyl vinyl ether copolymer, polyvinyl fluoride, a tetrafluoroethylene-ethylene copolymer, a tetrafluoroethylene-hexafluoropropylene copolymer, polychlorotrifluoroethylene, polyvinylidene fluoride, polyester, polycarbonate, polyurethane, polyimide, polyetherimide, polyimide and polypropylene.

In the organic EL device of the present invention, in order to improve stability against the temperature, the humidity and the environment, a protective layer can be provided on the surface of the device, and the whole part of the device can be protected by a silicon oil, a resin and the like. The respective layers of the organic EL device can be formed by applying any of a dry film forming method such as vacuum vapor deposition, sputtering, plasma and ion plating and a wet film forming method such as spin coating, dipping and flow coating. The film thickness shall not specifically be restricted, and it has to be set to a suited film thickness. If the film thickness is too large, large voltage has to be applied in order to obtain a constant light output, so that the efficiency is deteriorated. If the film thickness is too small, pinholes are formed, and the satisfactory light emitting luminance is not obtained when applying an electric field. Usually, the film thickness falls in a range of suitably 5 nm to 10 μm, preferably 10 nm to 0.2 μm.

In the case of the wet film forming method, materials for forming the respective layers are dissolved or dispersed in a suitable solvent such as ethanol, chloroform, tetrahydrofuran and dioxane to form thin films, and the solvent may be any one. Suitable resins and additives may be used in any organic thin film in order to improve the film forming property and prevent pinholes from being formed on the film. The resins which can be used include insulating resins such as polystyrene, polycarbonate, polyallylate, polyester, polyamide, polyurethane, polysulfone, polymethyl methacrylate, polymethyl acrylate and cellulose and copolymers thereof, photoconductive resins such as poly-N-vinylcarbazole and polysilane and conductive resins such as polythiophene and polypyrrole. The additives include antioxidants, UV absorbers and plasticizers.

The organic EL device of the present invention can be used, for example, as a plane luminant for flat panel displays of wall-mounted television sets, a backlight for copying machines, printers and liquid crystal displays, a light source for meters, a display board and a marker lamp.

EXAMPLES

Next, the present invention shall be explained in further details with reference to examples, but the present invention shall by no means be restricted by these examples.

Synthetic Example 1

Synthesis of Intermediate A

A three neck flask of 1000 ml was charged with 2-bromofluorene 100 g (manufactured by Tokyo Kasei Kogyo Co., Ltd.), dimethylsulfoxide (DMSO) 200 ml, benzyltriethylammonium chloride 1.9 g (manufactured by Wako Pure Chemical Industries Ltd.) and a sodium hydroxide aqueous solution of 50% by weight 130 g under argon atmosphere.

This reactor was put in a water bath, and 1,5-dibromopentane 88.1 g (manufactured by Wako Pure Chemical Industries Ltd.) was added thereto while stirring.

After reacted for 5 hours, 2000 ml of water was added, and the solution was extracted with 1000 ml of toluene. The organic layer was dried on magnesium sulfate, and the solvent was distilled off by means of a rotary evaporator to obtain 111 g of an oil which was the intended compound (yield: 91%).

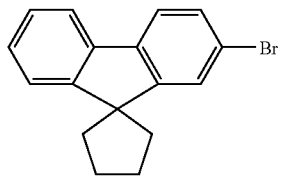

Intermediate A

Synthetic Example 2

Synthesis of Intermediate B

Reaction was carried out in the same manner as in Synthetic Example 1, except that 1,6-dibromohexane 93.5 g (manufactured by Wako Pure Chemical Industries Ltd.) was used in place of 1,5-dibromopentane to obtain 97 g of an oil which was the intended compound (yield: 76%)

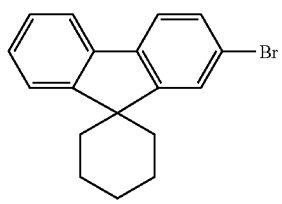

Intermediate B

Example 1

Synthesis of Compound (HT-01)

The intermediate (B) 1.2 g, N,N'-di(naphthyl-2-yl)-1,4-phenylenediamine 0.60 g (manufactured by Kanto Chemical Co., Inc.), sodium t-butoxide 1.2 g (manufactured by Hiroshima Wako Corporation), bis(triphenylphosphine)palladium (II) chloride 0.3 g (manufactured by Tokyo Kasei Kogyo Co., Ltd.) and xylene 300 ml were put under argon flow to react them at 130° C. for 24 hours.

After cooled down, 500 ml of water was added thereto, and the mixture was filtered through celite. The filtrate was extracted with toluene, and the extract was dried on anhydrous magnesium sulfate. This was concentrated under reduced pressure, and the resulting crude product was refined by means of a column and recrystallized from toluene. It was filtered and then dried to obtain 0.74 g of a pale yellow powder.

The powder thus obtained was identified as the compound (HT-01) (yield: 54%) by FD-MS (field desorption mass spectrum) analysis since a main peak of m/z=825 corresponding to $C_{62}H_{52}N_2$=824 was obtained. The glass transition temperature was 118° C.

Example 2

Synthesis of Compound (HT-02)

The intermediate (A) 1.2 g, N,N'-di(naphthyl-2-yl)-1,4-phenylenediamine 0.60 g (manufactured by Kanto Chemical Co., Inc.), sodium t-butoxide 1.2 g (manufactured by Hiroshima Wako Corporation), bis(triphenylphosphine)palladium (II) chloride 0.3 g (manufactured by Tokyo Kasei Kogyo Co., Ltd.) and xylene 300 ml were put under argon flow to react them at 130° C. for 24 hours.

After cooled down, 500 ml of water was added thereto, and the mixture was filtered through celite. The filtrate was extracted with toluene, and the extract was dried on anhydrous magnesium sulfate. This was concentrated under reduced pressure, and the resulting crude product was refined by means of a column and recrystallized from toluene. It was filtered and dried to obtain 0.87 g of a pale yellow powder.

The powder thus obtained was identified as the compound (HT-02) (yield: 66%) by FD-MS analysis since a main peak of m/z=797 corresponding to $C_{60}H_{48}N_2$=796 was obtained. The glass transition temperature was 117° C.

Example 3

Synthesis of Compound (HT-03)

The intermediate (B) 1.3 g, N,N-diphenyl-4,4'-benzidine 0.56 g (manufactured by Wako Pure Chemical Industries Inc.), sodium t-butoxide 1.2 g (manufactured by Hiroshima Wako Corporation), bis(triphenylphosphine)palladium (II) chloride 0.3 g (manufactured by Tokyo Kasei Kogyo Co., Ltd.) and xylene 300 ml were put under argon flow to react them at 130° C. for 24 hours.

After cooled down, 500 ml of water was added thereto, and the mixture was filtered through celite. The filtrate was extracted with toluene, and the extract was dried on anhydrous magnesium sulfate. This was concentrated under reduced pressure, and the resulting crude product was refined by means of a column and recrystallized from toluene. It was filtered and then dried to obtain 0.96 g of a pale yellow powder.

The powder thus obtained was identified as the compound (HT-03) (yield: 72%) by FD-MS analysis since a main peak of m/z=801 corresponding to $C_{60}H_{52}N_2$=800 was obtained. The glass transition temperature was 124° C.

Example 4

Synthesis of Compound (HT-04)

The intermediate (A) 1.2 g, N,N-diphenyl-4,4'-benzidine 0.56 g (manufactured by Wako Pure Chemical Industries Inc.), sodium t-butoxide 1.2 g (manufactured by Hiroshima Wako Corporation), bis(triphenylphosphine)palladium (II) chloride 0.3 g (manufactured by Tokyo Kasei Kogyo Co., Ltd.) and xylene 300 ml were put under argon flow to react them at 130° C. for 24 hours.

After cooled down, 500 ml of water was added thereto, and the mixture was filtered through celite. The filtrate was extracted with toluene, and the extract was dried on anhydrous magnesium sulfate. This was concentrated under reduced pressure, and the resulting crude product was refined by means of a column and recrystallized from toluene. It was filtered and then dried to obtain 0.94 g of a pale yellow powder.

The powder thus obtained was identified as the compound (HT-04) (yield: 73%) by FD-MS analysis since a main peak of m/z=772 corresponding to $C_{58}H_{48}N_2$=772 was obtained. The glass transition temperature was 124° C.

Example 5

Synthesis of Compound (HT-05)

The intermediate (B) 2.6 g, 4,4''-diamino-p-terphenylene 0.43 g (manufactured by Lancaster Co., Ltd.), sodium t-butoxide 2.0 g (manufactured by Hiroshima Wako Corporation), bis(triphenylphosphine)palladium (II) chloride 0.6 g (manufactured by Tokyo Kasei Kogyo Co., Ltd.) and xylene 300 ml were put under argon flow to react them at 130° C. for 24 hours.

After cooled down, 500 ml of water was added thereto, and the mixture was filtered through celite. The filtrate was extracted with toluene, and the extract was dried on anhydrous magnesium sulfate. This was concentrated under reduced pressure, and the resulting crude product was refined by means of a column and recrystallized from toluene. It was filtered and then dried to obtain 0.71 g of a pale yellow powder.

The powder thus obtained was identified as the compound (HT-05) (yield: 36%) by FD-MS analysis since a main peak of m/z=1189 corresponding to $C_{90}H_{80}N_2$=1188 was obtained. The glass transition temperature was 131° C.

Example 6

Synthesis of Compound (HT-06)

The intermediate (A) 2.4 g, 4,4"-diamino-p-terphenylene 0.43 g (manufactured by Lancaster Co., Ltd.), sodium t-butoxide 2.0 g (manufactured by Hiroshima Wako Corporation), bis(triphenylphosphine)palladium (II) chloride 0.6 g (manufactured by Tokyo Kasei Kogyo Co., Ltd.) and xylene 300 ml were put under argon flow to react them at 130° C. for 24 hours.

After cooled down, 500 ml of water was added thereto, and the mixture was filtered through celite. The filtrate was extracted with toluene, and the extract was dried on anhydrous magnesium sulfate. This was concentrated under reduced pressure, and the resulting crude product was refined by means of a column and recrystallized from toluene. It was filtered and then dried to obtain 0.77 g of a pale yellow powder.

The powder thus obtained was identified as the compound (HT-06) (yield: 41%) by FD-MS analysis since a main peak of m/z=1133 corresponding to $C_{86}H_{72}N_2$=1132 was obtained. The glass transition temperature was 132° C.

Synthetic Example 3

Synthesis of N,N-di-(4-biphenylyl)benzamide

A three neck flask of 100 ml was charged with 4-bromobiphenyl 10.0 g (manufactured by Tokyo Kasei Kogyo Co., Ltd.), benzamide 2.31 g (manufactured by Tokyo Kasei Kogyo Co., Ltd.), cuprous iodide 0.36 g (manufactured by Kanto Chemical Co., Inc.) and anhydrous potassium carbonate 5.8 g (manufactured by Kanto Chemical Co., Inc.). Further, a stirring rod was put therein, and rubber caps were set at both end necks of the flask. Set were a coiled tube for refluxing at the central neck, a three-way cock thereon and a balloon filled with argon gas, and the system was substituted three times with argon gas filled in the balloon by means of a vacuum pump.

Next, 50 ml of diethylbenzene was added thereto through a rubber septum by means of a syringe, and the flask was set on an oil bath. The temperature was gradually elevated up to 200° C. while stirring the solution. After 6 hours, the flask was removed from the oil bath to terminate the reaction, and it was left standing for 12 hours under argon atmosphere.

The reaction solution was transferred into a separating funnel, and 100 ml of dichloromethane was added thereto to dissolve the precipitate. The solution was washed with 60 ml of saturated brine, and then the organic layer was dried on anhydrous potassium carbonate. The solvent was distilled off from an organic layer obtained by filtering off potassium carbonate, and 200 ml of toluene and 40 ml of ethanol were added to the resulting residue. A drying tube was fitted thereto, and the solution was heated to 80° C. to completely dissolve the residue. Then, it was left standing for 12 hours and gradually cooled down to room temperature to thereby carry out recrystallization.

Crystal deposited was filtered and dried under vacuum at 60° C. to obtain 7.22 g of N,N-di-(4-biphenylyl)benzamide.

Synthetic Example 4

Synthesis of Intermediate C

A three neck flask of 1000 ml was charged with 2-bromofluorene 100 g (manufactured by Tokyo Kasei Kogyo Co., Ltd.), DMSO 200 ml, benzyltriethylammonium chloride 1.9 g (manufactured by Wako Pure Chemical Industries Ltd.) and a sodium hydroxide aqueous solution of 50% by weight 130 g under argon atmosphere.

This reactor was put in a water bath, and 1,2-dibenzyl bromide 108 g (manufactured by Wako Pure Chemical Industries Ltd.) was added thereto while stirring.

After reacted for 5 hours, 2000 ml f water was added thereto, and the solution was extracted with 1000 ml of toluene. The organic layer was dried on magnesium sulfate, and the solvent was distilled off by means of a rotary evaporator to obtain 105 g of an oil which was the intended compound (yield: 74%).

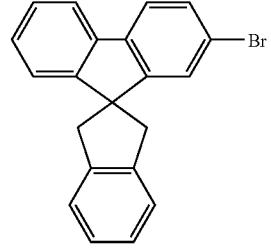

Intermediate C

Example 7

Synthesis of Compound (HT-07)

A two neck flask of 50 ml was charged with N,N-di-(4-biphenylyl)benzamide 1.00 g, the intermediate (C) 1.00 g, cuprous iodide 0.021 g and potassium hydroxide 0.51 g, and a rubber cap was mounted on one neck of the flask. Set were a coiled tube for refluxing at the central neck, a three-way cock thereon and a balloon filled with argon gas, and the system was substituted three times with argon gas filled in the balloon by means of a vacuum pump.

Next, 20 ml of xylene was added thereto through a rubber septum by means of a syringe, and the flask was set on an oil bath. The temperature was gradually elevated up to 140° C.

while stirring the solution. After stirring at 140° C. for 6 hours, the flask was removed from the oil bath and left standing for 12 hours at room temperature.

A precipitate deposited was completely dissolved in 50 ml of dichloromethane, and the solution was transferred into a separating funnel. The solution was washed with 50 ml of saturated brine, and then the organic layer separated was dried on anhydrous potassium carbonate. After filtering, the solvent was distilled off, and 150 ml of toluene and 50 ml of ethanol were added to the resulting residue. A drying tube was mounted thereon, and the solution was heated up to 80° C. to dissolve the precipitate. Then, it was gradually cooled down to room temperature. Next, the precipitate was filtered and washed with a small amount of toluene and ethanol, and then it was dried at 60° C. for 3 hours by means of a vacuum dryer to obtain 0.72 g of a yellow powder.

The powder thus obtained was identified as the compound (HT-07) (yield: 52%) by FD-MS analysis since a main peak of m/z=587 corresponding to $C_{45}H_{33}N=587$ was obtained. The glass transition temperature was 116° C.

Example 8

Production and Evaluation of Organic EL Device

A glass substrate (manufactured by Geomatec Co., Ltd.) of 25 mm×75 mm×1.1 mm thickness equipped with an ITO transparent electrode was subjected to supersonic wave washing in isopropyl alcohol for 5 minutes and then to UV ozone washing for 30 minutes.

The glass substrate equipped with an ITO transparent electrode line after washing was mounted on a substrate holder of a vacuum depositing apparatus, and a film of the following compound H232 having a film thickness of 60 nm was formed on a face at a side on which the transparent electrode line was formed so that the transparent electrode described above was covered. This H232 film functions as a hole injecting layer. Next, a film of the compound (HT-01) having a film thickness of 20 nm described above was formed on the H232 film. This film functions as a hole transporting layer.

Further, the following compound EM1 was deposited as a host material to form a film having a film thickness of 40 nm. The following amine compound D1 having a styryl group was deposited as a luminescent dopant at the same time as above so that a weight ratio of EM1 to D1 was 40:2. This film functions as a luminescent layer.

A film of the following compound Alq having a film thickness of 20 nm was formed on the above film. This film functions as an electron injecting layer. Further, an LiF film (film thickness: 1 nm) was formed as an electron injecting layer (or a cathode). Metal Al was deposited on this LiF film to form a metal cathode, whereby an organic EL device was produced.

This device was subjected to a current-carrying test to obtain blue luminescence having a light emitting luminance of 153 nit, a maximum light emitting luminance of 50,000 nit and a luminous efficiency of 4.8 cd/A at a direct current voltage of 6 V. Further, it was stored in an atmosphere of 105° C. for 500 hours to carry out a heat resistance storage test. A direct current voltage of 6 V was applied as was the case with before the test to find that a luminance of 98% (luminance preserving rate: 98%) based on the initial luminance was shown.

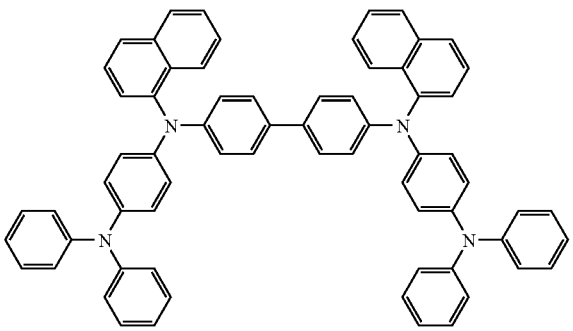

H232

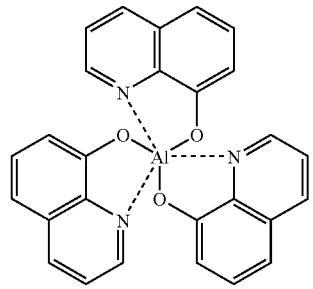

Alq

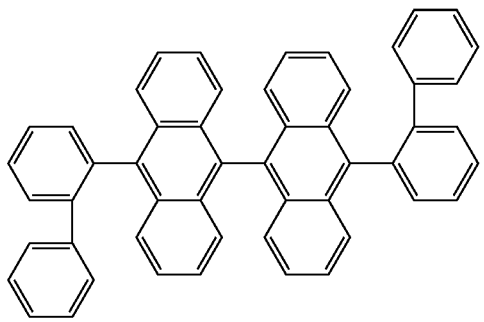

EM1

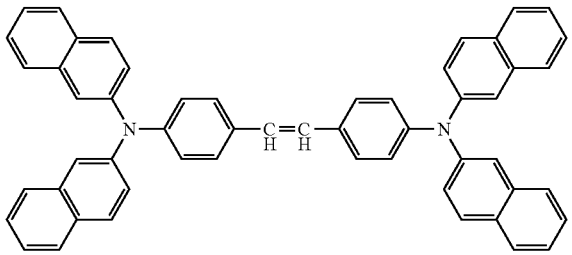

D1

Examples 9 to 13

Production and Evaluation of Organic EL Devices

Organic EL devices were produced in the same manner as in Example 8, except that in Example 8, compounds shown in Table 1 were used in place of the compound (HT-01), and the current-carrying test and the heat resistance storage test were carried out in the same manner as in Example 8. The results thereof are shown in Table 1.

Comparative Example 1

Production and Evaluation of Organic EL Device

An organic EL device was produced in the same manner as in Example 8, except that in Example 8, the following compound TPAF (glass transition temperature: lower than 100° C.) was used in place of the compound (HT-01), and the current-carrying test and the heat resistance storage test were carried out in the same manner as in Example 8. The results thereof are shown in Table 1.

TPAF

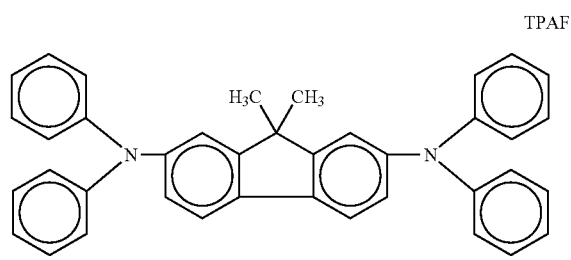

Comparative Example 2

Production and Evaluation of Organic EL Device

An organic EL device was produced in the same manner as in Example 8, except that in Example 8, N,N'-di(4-biphenyl)-N,N'-[2-(9,9-dimethylfluorenyl)]-4,4'-diaminobiphenyl (DFDBBZ shown below) (glass transition temperature: lower than 100° C.) was used in place of the compound (HT-01), and the current-carrying test and the heat resistance storage test were carried out in the same manner as in Example 8. The results thereof are shown in Table 1.

As shown in Table 1, TPAF used in Comparative Example 1 is poor in a heat resistance because of a low glass transition temperature, and the luminance after stored at 105° C. for 500 hours is lowered down to 10% of the luminance before storing.

DFDBBZ used in Comparative Example 2 has a high glass transition temperature and is satisfactory in a heat resistance. However, it has a high flatness in an end part having a fluorene skeleton and therefore brings about exciplex with the luminescent material. Accordingly, it is considered that the luminescent color is shifted to a longer wavelength and reduced in efficiency.

On the other hand, the organic EL devices produced in Examples 8 to 13 using the arylamine compounds according to the present invention are improved in a light emitting luminance and a luminous efficiency and excellent in a heat resistance. This is considered to be attributable to the facts that the arylamine compounds according to the present invention have a high glass transition temperature of 100° C. or higher due to a fluorene skeleton having a specific structure and that the cyclic structure introduced into the end makes it less liable to bring about exciplex with the luminescent layer.

Example 14

Production and Evaluation of Organic EL Device

An organic EL device was produced in the same manner as in Example 8, except that in Example 8, Alq and rubrene were deposited in a weight ratio of 30:1 in place of the compounds EM1 and D1 to form a film having a film thickness of 40 nm.

This device was subjected to a current-carrying test to obtain blue luminescence having a light emitting luminance of 1,300 nit, a maximum light emitting luminance of 98,000 nit and a very high luminous efficiency of 9.5 cd/A at a direct

DFDBBZ

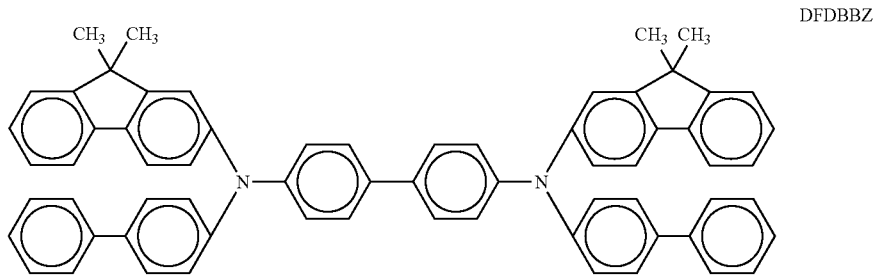

TABLE 1

| | Hole transporting material | Light emitting luminance (voltage 6 V) (nit) | Luminous efficiency (cd/A) | Luminescent color | Luminance preserving rate after stored at 105° C. for 500 hours (%) |
|---|---|---|---|---|---|
| Example 8 | HT-01 | 153 | 4.8 | Blue | 98 |
| Example 9 | HT-02 | 147 | 4.7 | Blue | 99 |
| Example 10 | HT-03 | 158 | 5.1 | Blue | 99 |
| Example 11 | HT-04 | 159 | 5.1 | Blue | 98 |
| Example 12 | HT-05 | 162 | 5.2 | Blue | 98 |
| Example 13 | HT-06 | 161 | 4.7 | Blue | 98 |
| Comparative Example 1 | TPAF | 138 | 4.4 | Blue | 10 |
| Comparative Example 2 | DFDBBZ | 128 | 2.2 | Yellow | 82 | current voltage of 6 V. Further, it was stored in an atmosphere of 105° C. for 500 hours to carry out a heat resistance storage test. A direct current voltage of 6 V was applied as was the case with before the test to find that a luminance of 99% (luminance preserving rate: 99%) based on the initial luminance was shown.

Further, the device was operated in an initial luminance of 1,000 nit at a constant current to carry out a life test to find that the half life was as very long as 6,900 hours. It can be found from the above matters that the arylamine compound of the present invention is very excellent as a hole transporting compound Comparative Example 3

Production and Evaluation of Organic EL Device

An organic EL device was produced in the same manner as in Example 14, except that in Example 14, DFDBBZ was used in place of the compound (HT-01). This device was operated in an initial luminance of 1,000 nit at a constant current to carry out a life test to find that the half life was as short as 1,850 hours.

Example 15

Production and Evaluation of Organic EL Device

An organic EL device. was produced in the same manner as in Example 11, except that in Example 11, only Alq was deposited in place of the compounds EM1 and D1 used for the luminescent layer to form a film having a film thickness of 40 nm. A luminescent dopant was not used.

The device thus obtained was subjected to the current-carrying test and the heat resistance storage test in the same manner as in Example 8, and the results thereof are shown in Table 2.

Comparative Example 4

Production and Evaluation of Organic EL Device

An organic EL device was produced in the same manner as in Example 15, except that in Example 15, the compound DFDBBZ was used in place of the compound HT-04. A luminescent dopant was not used.

The device thus obtained was subjected to the current-carrying test and the heat resistance storage test in the same manner as in Example 8, and the results thereof are shown in Table 2.

As shown in Table 2, the device using the compound DFDBBZ used in Comparative Example 4 has a low initial luminous efficiency as compared with that of the device produced in Example 15 using HT-04. Further, the preserving rate after stored at high temperature is 90% or lower. It is considered that DFDBBZ provides the device with a low efficiency and a low luminance preserving rate due to any interaction.

Example 17

An organic EL device was produced in the same manner as in Example 8, except that in Example 8, used were the following compound CBP in place of the compound EM1 used for the luminescent layer and the compound Ir(ppy)$_3$ described above in place of the compound D1 and that the following compound BAlq for forming a film having a film thickness of 10 nm and then the compound Alq for forming a film having a film thickness of 20 nm were deposited in place of depositing the compound Alq in the electron injecting layer to form a film having a film thickness of 20 nm.

The device thus obtained was measured for a luminous efficiency at a direct current voltage of 6 V to find that it was 34 cd/A.

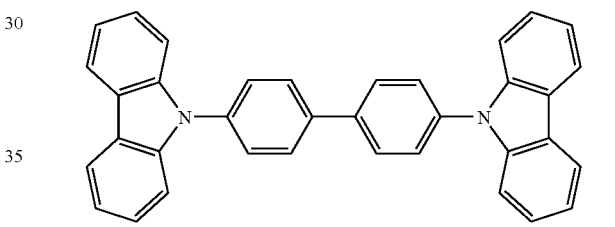

CBP

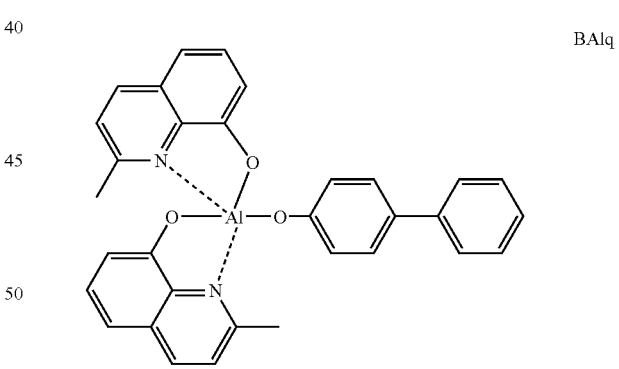

BAlq

TABLE 2

| | Hole transporting material | Light emitting luminance (voltage 6 V) (nit) | Luminous efficiency (cd/A) | Luminescent color | Luminance preserving rate after stored at 105° C. for 500 hours (%) |
|---|---|---|---|---|---|
| Example 15 | HT-04 | 115 | 3.6 | Yellowish green | 110 |
| Comparative Example 4 | DFDBBZ | 121 | 2.4 | Yellowish green | 87 |

Comparative Example 5

Production and Evaluation of Organic EL Device

An organic EL device was produced in the same manner as in Example 17, except that in Example 17, the following compound NPD was used in place of the compound HT-01. A luminescent dopant was not used.

The device thus obtained was measured for a luminous efficiency at a direct current voltage of 6 V to find that it was 26 cd/A.

NPD

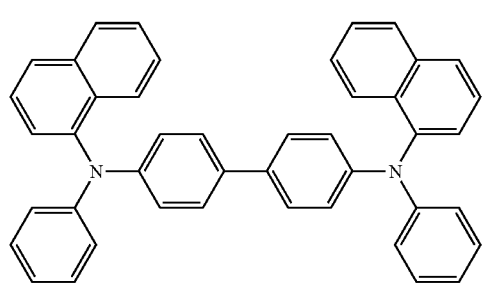

INDUSTRIAL APPLICABILITY

The organic EL device using the novel arylamine compound of the present invention has a high luminance, a high heat resistance and a long life, and it is excellent in a hole transporting property and has a high luminous efficiency. Accordingly, the organic EL device of the present invention is useful as a plane luminant for wall-mounted television sets and a backlight for displays.

What is claimed is:

1. An arylamine compound represented by the following Formula (1):

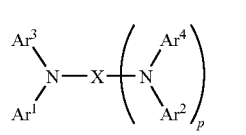

(1)

wherein X is a substituted or non-substituted aromatic hydrocarbon group having 6 to 40 carbon atoms or a substituted or non-substituted heterocyclic group having 5 to 40 carbon atoms; $Ar^1$, $Ar^2$, $Ar^3$ and $Ar^4$ each are independently a substituted or non-substituted group having 6 to 40 carbon atoms or a substituted or non-substituted heterocyclic group having 5 to 40 carbon atoms; provided that at least two of $Ar^1$, $Ar^2$, $Ar^3$ and $Ar^4$ is a group represented by the following Formulae (1-1) to (1-15); $Ar^1$, $Ar^2$, $Ar^3$ and $Ar^4$ may be the same as or different from each other, and they may be combined with adjacent ones to form a saturated or unsaturated ring; and p is an integer of 1 or 2:

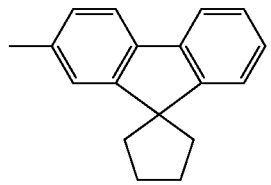
(1-1)

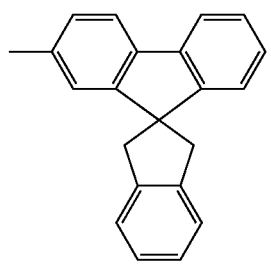
(1-2)

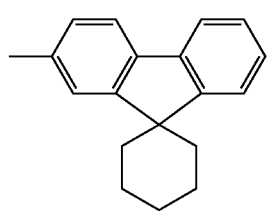
(1-3)

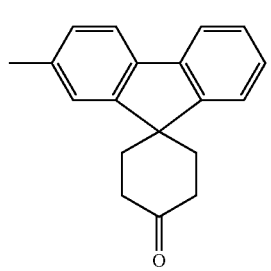
(1-4)

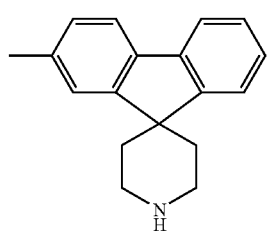
(1-5)

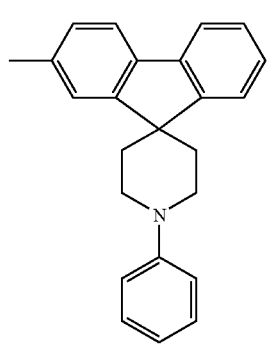
(1-6)

-continued (1-7) 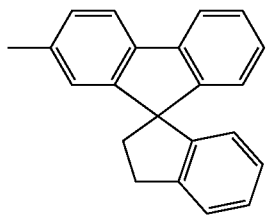

(1-8) 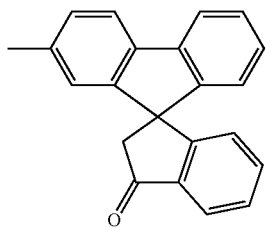

(1-9) 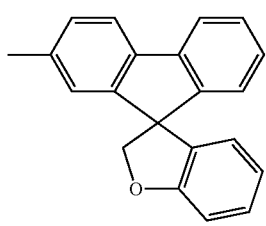

(1-10) 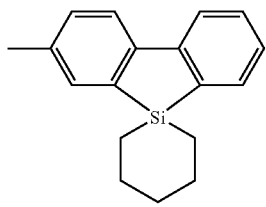

(1-11) 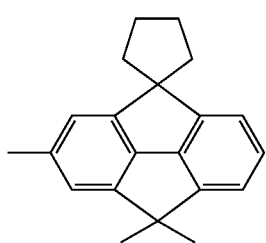

(1-12) 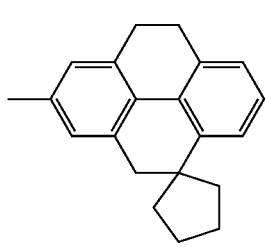

-continued (1-13) 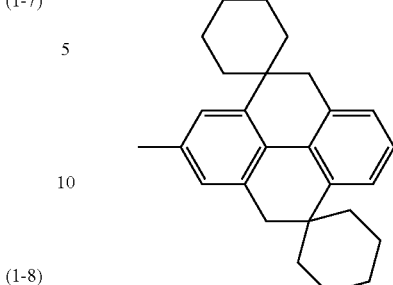

(1-14) 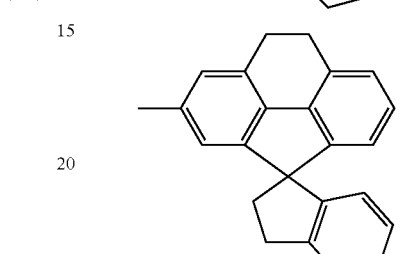

(1-15) 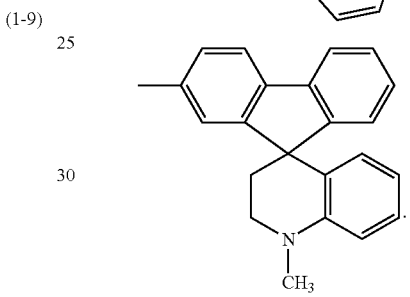

2. The aryl amine compound as described in claim 1, wherein in Formula (1) described above, the aromatic hydrocarbon group represented by X is a monovalent, divalent or trivalent residue of benzene, biphenyl, terphenyl, naphthalene, fluorene, pyrene, spirobifluorene or stilbene.

3. The aryl amine compound as described in claim 1, wherein in Formula (1) described above, the aryl group represented by $Ar^1$ to $Ar^4$ each are independently phenyl or a polycyclic aromatic group.

4. The aryl amine compound as described in claim 1, being a material for an organic electroluminescent device.

5. The aryl amine compound as described in claim 1, being a hole transporting material for an organic electroluminescent device.

6. An organic electroluminescent device in which an organic compound layer comprising one layer or plural layers including at least a luminescent layer is interposed between a cathode and an anode, wherein at least one of the above organic compound layers contains the arylamine derivative as described in claim 1.

7. The organic electroluminescent device as described in claim 6, wherein the luminescent layer comprises the arylamine derivative.

8. The organic electroluminescent device as described in claim 6, wherein the luminescent layer described above has a hole transporting layer, and the above hole transporting layer contains the arylamine derivative.

9. An organic electroluminescent device in which an organic compound layer comprising one layer or plural layers including at least a luminescent layer is interposed between a cathode and an anode, wherein at least one of the above organic compound layers contains the arylamine derivative as described in claim 1 and a luminescent material.

10. An organic electroluminescent device in which an organic compound layer comprising one layer or plural layers including at least a luminescent layer is interposed between a cathode and an anode, wherein the above organic compound layer is prepared by laminating a hole transporting layer containing the arylamine derivative as described in claim 1 and a luminescent layer comprising a phosphorescence-emitting metal complex and a host material.

* * * * *